United States Patent

Chaudhari et al.

(10) Patent No.: US 6,815,447 B2
(45) Date of Patent: Nov. 9, 2004

(54) N-TYPE CALCIUM CHANNEL ANTAGONISTS FOR THE TREATMENT OF PAIN

(75) Inventors: Bipinchandra Chaudhari, Wilmington, DE (US); Marc Chapdelaine, Wilmington, DE (US); Greg Hostetler, Newark, DE (US); Lucius Kemp, Philadelphia, PA (US); John McCauley, Wilmington, DE (US)

(73) Assignee: Astrazeneca AB, Sodertalje (SE)

( * ) Notice: Subject to any disclaimer, the term of this patent is extended or adjusted under 35 U.S.C. 154(b) by 0 days.

(21) Appl. No.: 10/415,785

(22) PCT Filed: Oct. 31, 2001

(86) PCT No.: PCT/SE01/02388

§ 371 (c)(1),
(2), (4) Date: Oct. 2, 2003

(87) PCT Pub. No.: WO02/36586

PCT Pub. Date: May 10, 2002

(65) Prior Publication Data

US 2004/0058945 A1 Mar. 25, 2004

(30) Foreign Application Priority Data

Nov. 6, 2000 (SE) .............................. 0004053

(51) Int. Cl.$^7$ ..................... C07D 401/12; A61K 31/506
(52) U.S. Cl. ....................................... 514/275; 544/324
(58) Field of Search .......................... 544/324; 514/275

(56) References Cited

FOREIGN PATENT DOCUMENTS

| EP | 1072263 A1 | 1/2001 |
|---|---|---|
| GB | 794043 | 4/1958 |

*Primary Examiner*—Deepak Rao
(74) *Attorney, Agent, or Firm*—Kenneth F. Mitchell

(57) ABSTRACT

Compounds useful for the treatment of pain in accord with the following structural diagram,

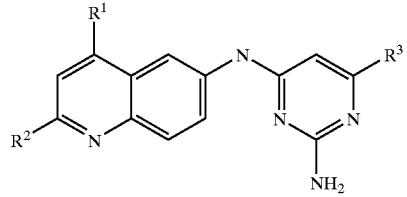

wherein $R^1$, $R^2$ and $R^3$ are any of a number of groups as defined in the specification and pharmaceutical compositions and methods of treatment utilising such compounds.

5 Claims, No Drawings

N-TYPE CALCIUM CHANNEL ANTAGONISTS FOR THE TREATMENT OF PAIN

FIELD OF THE INVENTION

This invention relates to compounds and methods for the treatment or prevention of pain or nociception.

RELATED ART

Pain causes a great deal of suffering and is a sensory experience distinct from sensations of touch, pressure, heat and cold. It is often described by sufferers by such terms as bright, dull, aching, pricking, cutting or burning and is generally considered to include both the original sensation and the reaction to that sensation. This range of sensations, as well as the variation in perception of pain by different individuals, renders a precise definition of pain difficult. Where pain is "caused" by the stimulation of nociceptive receptors and transmitted over intact neural pathways, this is termed nociceptive pain. Pain may also be caused by damage to neural structures, and pain is often is manifested as neural supersensitivity; this type of pain is referred to as neuropathic pain.

The level of stimulation at which pain is perceived is referred to as the "pain threshold". Where the pain threshold is raised, for instance, by the administration of an analgesic drug, a greater intensity or more prolonged stimulus is required before pain is experienced. Analgesics are a class of pharmaceutical agent which, following administration to a patient in need of such treatment, relieve pain without loss of consciousness. This is in contrast to other pain-relieving drugs, for example, general anaesthetics which obtund pain by producing a hiatus in consciousness, or local anaesthetics which block transmission in peripheral nerve fibres thereby preventing pain.

Tachykinin antagonists have been reported to induce antinociception in animals, which is believed to be analogous to analgesia in man (for review see Maggi et al, J. Auton. Pharmacol. (1993) 13, 23–93). In particular, non-peptide NK-I receptor antagonists have been shown to produce such analgesia, thus, for example, in classical tests of chemo-nociception (phenylbenzoquinone-induced writhing and formalin test) the NK-1 receptor antagonist RP 67,580 produced analgesia with potency comparable to that of morphine (Garret et al, Proc. Natl. Acad. Sci. USA (1993) 88, 10208–10212).

Opioid analgesics are a well-established class of analgesic agents. These compounds are generally accepted to include, in a generic sense, all drugs, natural or synthetic, with morphine-like actions. The synthetic and semi-synthetic opioid analgesics are derivatives of five chemical classes of compound: phenanthrenes; phenylheptylamines; phenylpiperidines; morphinans; and benzomorphans. Pharmacologically these compounds have diverse activities, thus some are strong agonists at the opioid receptors (e.g. morphine); others are moderate to mild agonists (e.g. codeine); still others exhibit mixed agonist-antagonist activity (e.g. nalbuphine); and yet others are partial agonists (e.g. nalorphine). Whilst an opioid partial agonist such as nalorphine, (the N-alkyl analogue of morphine) will antagonise the analgesic effects of morphine, when given alone it can be a potent analgesic in its own right. Of all of the opioid analgesics, morphine remains the most widely used and is a suitable archetype compound. Unfortunately, apart from its useful therapeutic properties, morphine also has a number of drawbacks including respiratory depression, decreased gastrointestinal motility (resulting in constipation) and, in some individuals, nausea and vomiting may occur. Another characteristic is the development of tolerance and physical dependence which may limit the clinical use of such compounds.

Anti-inflammatory compounds directed at blocking or reducing synovial inflammation, and thereby improving function, and analgesics directed to reducing pain, are presently the primary method of treating the rheumatoid diseases and arthritis. Aspirin and other salicylate compounds are frequently used in treatment to interrupt amplification of the inflammatory process and temporarily relieve the pain. Other drug compounds used for these purposes include phenylpropionic acid derivatives such as Ibuprofen and Naproxin, Sulindac, phenyl butazone, corticosteroids, antimalarials such as chloroquine and hydroxychloroquine sulfate, and fenemates. For a thorough review of various drugs utilized in treating rheumatic diseases, reference is made to J. Hosp. Pharm., 36:622 (May 1979).

Calcium channels are membrane-spanning, multi-subunit proteins that allow controlled entry of $Ca^{++}$ ions into cells from the extracellular fluid. Such channels are found throughout the animal kingdom, and have been identified in bacterial, fungal and plant cells. Commonly, calcium channels are voltage dependent. In such channels, the "opening" allows an initial influx of $Ca^{++}$ ions into the cells which lowers the potential difference between the inside of the cell bearing the channel and the extracellular medium bathing the cell. The rate of influx of $Ca^{++}$ ions into the cell depends on this potential difference. All "excitable" cells in animals, such as neurons of the central nervous system ("CNS"), peripheral nerve cells, and muscle cells, including those of skeletal muscles, cardiac muscles, and venous and arterial smooth muscles, have voltage-dependent calcium channels. Calcium channels are physiologically important because the channels have a central role in regulating intracellular $Ca^{++}$ ions levels. These levels are important for cell viability and function. Thus, intracellular $Ca^{++}$ ion concentrations are implicated in a number of vital processes in animals, such as neurotransrmitter release, muscle contraction, pacemaker activity, and secretion of hormones.

It is believed that calcium channels are relevant in certain disease states. A number of compounds useful in treating various cardiovascular diseases in animals, including humans, are thought to exert their beneficial effects by modulating functions of voltage-dependent calcium channels present in cardiac and/or vascular smooth muscle. Many of these compounds bind to calcium channels and block, or reduce the rate of, influx of $Ca^{++}$ ions into the cells in response to depolarization of the cell membrane. An understanding of the pharmacology of compounds that interact with calcium channels in other organ systems, such as the central nervous system, and the ability to rationally design compounds that will interact with these specific subtypes of human calcium channels to have desired therapeutic, e.g., treatment of neurodegenerative disorders, effects have been hampered by an inability to independently determine how many different types of calcium channels exist or the molecular nature of individual subtypes, particularly in the CNS, and the unavailability of pure preparations of specific channel subtypes, i.e., systems to evaluate the specificity of calcium channel-effecting compounds.

Multiple types of calcium channels have been detected based on electrophysiological and pharmacological studies of various mammalian cells from various tissues (e.g., skeletal muscle, cardiac muscle, lung, smooth muscle and brain) Bean, B. P., Annu Rev. Physiol. 51:367–384 (1989) and Hess, P., Annu. Rev. Neurosci. 56:337 (1990). These different types of calcium channels have been broadly categorized into four classes, L-, T-, N-, and P-type, distinguished by current kinetics, holding potential sensitivity and sensitivity to calcium channel agonists and antagonists. Four subtypes of neuronal voltage-dependent calcium channels have been proposed Swandulla, D. et al., Trends Neurosci 14:46 (1991). The L-, N- and P-type channels have each been implicated in nociception, but only the N-type channel has been consistently implicated in acute, persistent and neuropathic pain. A synthetic version of Ω-conotoxin MVIIA, a 25-amino acid peptide derived from the venom of the piscivorous marine snail, Conus magus has been used intrathecally in humans and has ~85% success rate for the treatment of pain with a greater potency than morphine.

While known drug therapies have utility, there are drawbacks to their use. For instance, it may take up to six months of consistent use of some medications in order for the product to have effect in relieving the patient's pain. Consequently, a particular subject may be receiving treatment and continuing to suffer for up to six months before the physician can assess whether the treatment is effective. Many existing drugs also have substantial adverse side effects in certain patients, and subjects must therefore be carefullly monitored. Additionally, most existing drugs bring only temporary relief to sufferers and must be taken consistently on a daily or weekly basis for continued relief. Finally, with disease progression, the amount of medication needed to alleviate the pain may increase thus increasing the potential for side effects. Thus, there is still a need for an effective and safe treatment to alleviate pain.

SUMMARY OF THE INVENTION

In one aspect the present invention provides compounds having selective action at N-type calcium channels that are useful for the treatment of pain.

Compounds of the present invention that show selective action at N-type calcium channels are compounds in accord with structural diagram I,

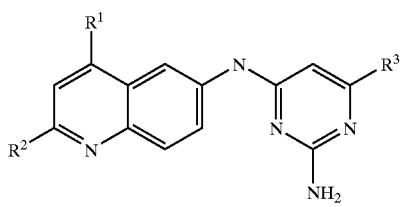

I wherein:
$R^1$ is $NE^1E^2$ where $E^1$ is selected from hydrogen and methyl and $E^2$ is selected from hydrogen, $C_{1-4}$alkyl and phenyl$C_{1-4}$alkyl;
$R^2$ is selected from $E^3$ and $E^4$, wherein:
$E^3$ is selected from $C_{1-6}$alkyl, $C_{1-4}$alkoxy and $C_{1-6}$alkoxy$C_{1-4}$alkyl; and
$E^4$ is phenyl substituted with a moiety selected from halogen, $C_{1-4}$alkyl, $C_{1-4}$alkoxy, perfluoro$C_{1-2}$alkyl and $C_{5-7}$cycloalkyl;
$R^3$ is selected from $E^5$ and $E^6$, wherein:
$E^5$ is selected from $NH_2$, perfluoro$C_{1-2}$alkyl, $C_{1-6}$alkyl, $C_{1-6}$alkoxy$C_{1-4}$alkyl, phenyl$C_{1-2}$alkoxy and phenoxy$C_{1-2}$alkyl; and
$E^6$ is phenyl substituted at one or two positions with moieties independently selected from halogen, cyano, perfluoro$C_{1-2}$alkyl, $C_{1-4}$alkoxy, phenyl$C_{1-2}$alkoxy, phenoxy$C_{1-2}$alkyl, $C_{1-6}$alkoxy$C_{1-4}$alkyl.

Particular compounds of the invention are those wherein:
$R^1$ is $NE^1E^2$ where $E^1$ is hydrogen and $E^2$ is selected from hydrogen, methyl and benzyl;
$R^2$ is selected from $E^3$ and $E^4$, wherein:
$E^3$ is selected from methyl, pentyl, propoxymethyl; and
$E^4$ is phenyl substituted with a moiety selected from fluoro, chloro, methyl, methoxy, trifluoromethyl and cyclohexyl;
$R^3$ is selected from $E^5$ and $E^6$, wherein:
$E^5$ is selected from methyl, pentyl, trifluoromethyl, propoxymethyl, benzyloxy and phenyloxymethyl; and
$E^6$ is phenyl substituted at one or two positions with moieties independently selected from chloro, fluoro, butyl, trifluoromethyl, methoxy, ethoxy, benzyloxy, phenoxymethyl, propoxymethyl and cyano.

Most particular compounds of the invention are those exemplified herein.

In another aspect, the invention comprises a method for using compounds according to structural diagram I for the treatment of pain, said method comprising administering a pain-ameliorating effective amount of any such compound.

One embodiment of the method of the invention comprises administering a pain-ameliorating effective amount of a compound in accordance with structural diagram I to a subject in need of treatment for acute, persistent or neuropathic pain.

In a further aspect, the invention comprises methods for making compounds in accord with structural diagram I.

In yet another aspect, the invention comprises pharmaceutical compositions comprising compounds in accord with structural diagram I together with excipients, diluents or stabilisers, as further disclosed herein, useful for the treatment of acute, persistent and neuropathic pain.

DETAILED DESCRIPTION OF THE INVENTION

Compounds of the invention are those within the scope of the generic description and particularly those compounds exemplified hereafter.

Suitable pharmaceutically-acceptable salts of compounds of the invention include acid addition salts such as methanesulphonate, fumarate, hydrochloride, hydrobromide, citrate, tris(hydroxymethyl)aminomethane, maleate and salts formed with phosphoric and sulphuric acid.

Where compounds of the present invention possess a chiral center it is to be understood that the invention encompasses all optical isomers and diastereoisomers of such compounds.

Where compounds of the present invention can tautomerize it is to be understood that the invention encompasses all tautomeric forms of such compounds.

Where compounds of the present invention can exist in unsolvated as well as solvated forms such as, for example, hydrated forms, it is to be understood that the invention encompasses all such solvated and unsolvated forms.

Another aspect of the invention provides processes for making compounds of the invention. Generally, compounds of the invention were prepared by preparing chloro-pyrimidine or triflate-pyrimidine precursors from hydroxy-pyrimidine precursors, and reacting said chloro-pyrimidine or triflate-pyrimidine precursors with quinoline precursors to form pyrimidyl-quinoline compounds of the invention.

a) Hydroxy-pyrimidine precursors were prepared by reacting a 3-substituted-3-oxo-propionic ethyl ester with guanidine hydrochloride in N-dimethylformamide in the presence of sodium hydride and activated 5 Å molecular seives.

b) Chloro-pyrimidine precursors were prepared by chlorinating a hydroxy-pyrimidine compound according to structural diagram II by refluxing with phosphoryloxychloride and phosphorus pentachloride to form a compound in according to structural diagram III,

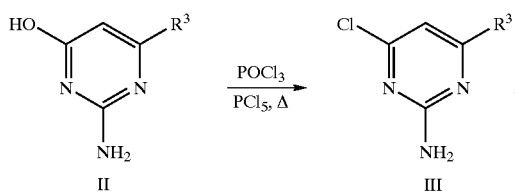

c) Triflate-pyrimidine precursors were prepared by reacting a hydroxy-pyrimidine compound according to structural diagram II by heating with N-phenyl trifluoromethane sulfonamide, triethylamine and dry N-methyl-2-pyrolidinone to form a compound in according to structural diagram IV,

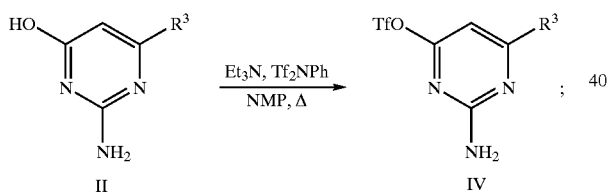

d) Novel precursor quinolines were prepared according to the following process:

d1) preparing novel 3-substituted-3-oxo-propionic acid ethyl esters (β-keto esters) according to structural diagram V, as follows:

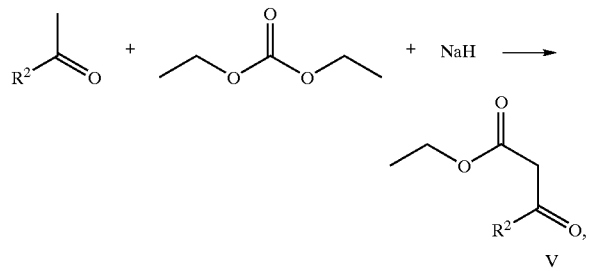

wherein $R^2$ is as heretofore defined;

d2) converting said β-keto esters of structural diagram V to enamines according to structural diagram. VI, as follows

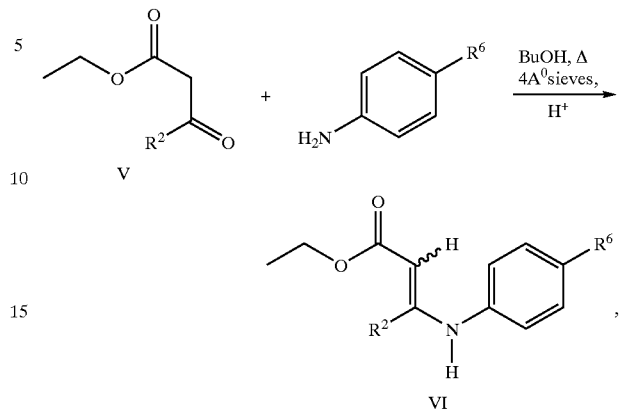

wherein $R^6$ is a group selected from —NH—CO—CH$_3$ or NO$_2$;

d3) cyclizing said enamines of structural diagram VI to form compounds according to structural diagram VII, as follows

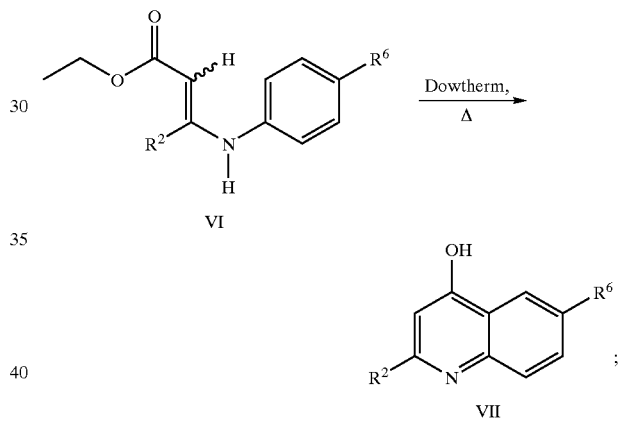

and d4) when $R^6$ is —NH—CO—CH$_3$, converting a compound of structural diagram VII to a compound according to structural diagram I by the process of the following scheme:

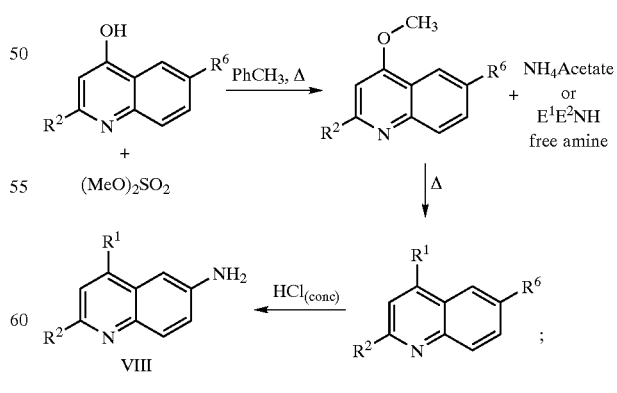

or, when $R^6$ is —NO$_2$, converting a compound of structural diagram VII to a compound according to structural diagram I as follows:

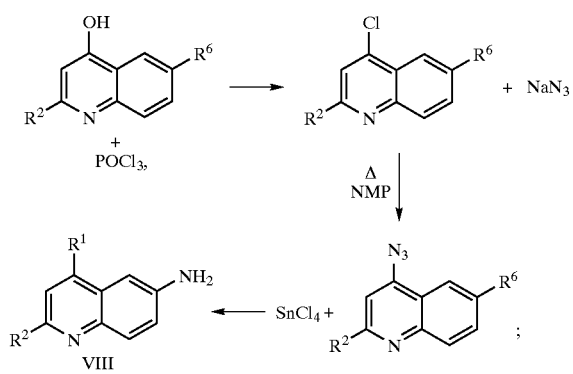

or, alternatively,
when $R^6$ is —$NO_2$, converting a compound of structural diagram VII to a compound according to structural diagram I as follows:

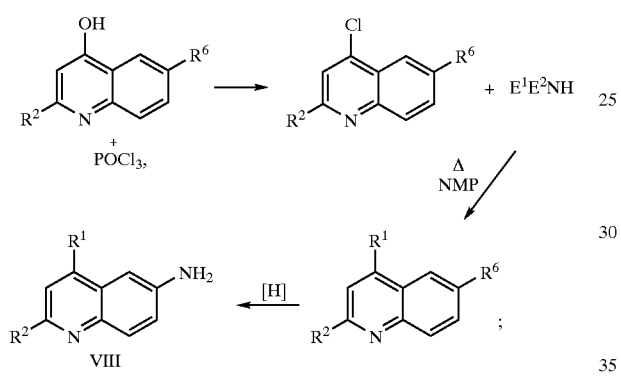

e) reacting a quinoline precursor of structure VIII with a chloro-pyrimidine precursor of structure III according to the following scheme to form a compound according to structural diagram I:

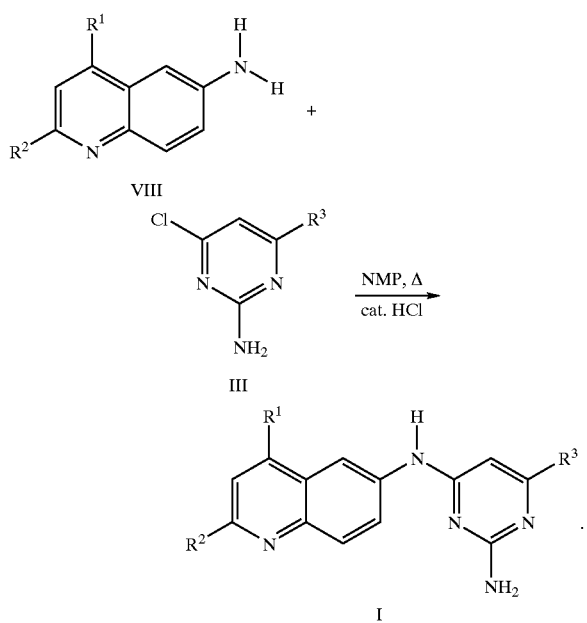

or, f) reacting a quinoline precursor of structure VIII with a triflate-pyrimidine precursor of structure IV according to the following scheme to form a compound according to structural diagram I:

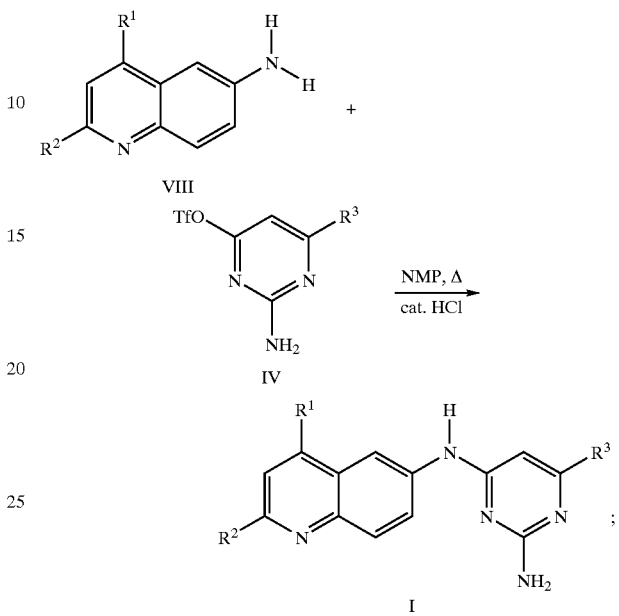

wherein, if necessary, in steps a), b), c), d), e) and f) any functional group is protected with a protecting group, and thereafter, g) removing any said protecting group;

h) converting one compound according to structural diagram I to another compound according to structural diagram I by procedures described in Methods A through L herein, and i) purifying said compound of structural diagram I to the extent necessary and, if necessary, forming a pharmaceutically-acceptable salt.

To use a compound of the invention or a pharmaceutically-acceptable salt thereof for the therapeutic treatment, which may include prophylactic treatment, of pain in mammals, which may be humans, the compound can be formulated in accordance with standard pharmaceutical practice as a pharmaceutical composition. Accordingly, a further aspect of the invention provides a pharmaceutical composition which contains a compound of the structural diagram I as defined herein or a pharmaceutically-acceptable salt thereof, in association with a pharmaceutically-acceptable additive such as an excipient or carrier.

Suitable pharmaceutical compositions that contain a compound of the invention may be administered in conventional ways, for example by oral, topical, parenteral, buccal, nasal, vaginal or rectal administration, or by inhalation. For these purposes a compound of the invention may be formulated by means known in the art in the form of, for example, tablets, capsules, aqueous or oily solutions, suspensions, emulsions, creams, ointments, gels, nasal sprays, suppositories, finely divided powders or aerosols for inhalation, and for parenteral use (including intravenous, intramuscular or infusion) sterile aqueous; or oily solutions or suspensions or sterile emulsions. A preferred route of administration is orally by tablet or capsule.

In addition to a compound of the present invention, a pharmaceutical composition of this invention may also contain one or more other pharmacologically-active agents. Alternatively, a pharmaceutical composition comprising a compound of this invention may be co-administered simultaneously or sequentially with one or more other compatible pharmacologically-active agents.

Pharmaceutical compositions of this invention will normally be administered so that a pain-ameliorating effective daily dose is received by the subject. The daily dose may be given in divided doses as necessary, the precise amount of the compound received and the route of administration depending on the weight, age and sex of the patient being treated and on the particular disease condition being treated according to principles known in the art. A preferred dosage regime is once daily.

A yet further embodiment of the invention provide the use of a compound of the structural diagram I, or a pharmaceutically-acceptable salt thereof, in the manufacture of a medicament useful for binding to N-type calcium channels in a warm-blooded animal such as a human being.

Still another embodiment of the invention provides a method of binding a compound of the invention to N-type calcium channels of a warm-blooded animal, such as a human being, in need of treatment for pain, which method comprises administering to said animal an effective amount of a compound of structural diagram I or a pharmaceutically-acceptable salt thereof.

A further aspect of the present invention provides a pharmaceutical composition which includes a compound of the present invention as defined herein or a pharmaceutically-acceptable salt thereof, in association with a pharmaceutically-acceptable additive such as an excipient or a carrier.

A still further aspect of the present invention is a method of treatment of the human or animal body that includes the administration of a compound of the present invention or a pharmaceutically-acceptable salt thereof.

Definitions:

When used herein "halo" or "halogen" means fluoro, chloro, bromo or iodo;

when substituents herein are stated to be "selected from" or "independently selected from" a group of moieties, it is to be understood that included compounds are those where all substituents are the same and compounds where each substituent is different;

when used herein the term "allyl," as in for example $C_1$-alkyl, unless otherwise defined, includes both straight and branched chain alkyl groups. References to individual alkyl groups such as "propyl" mean the normal, straight chain form, that is, n-propyl;

when used herein, a term such as "$C_{1-6}$alkyl" means alkyl groups having 1, 2, 3, 4, 5 or 6 carbon atoms and collective groups such as $C_{1-4}$alkyl and includes straight and branched moieties such as methyl, ethyl, iso-propyl and t-butyl, similarly, a term such as "$C_{1-3}$alkoxy" includes particular moieties such as methoxy, ethoxy and propoxy, and terms used herein that are not otherwise defined are intended to have their conventionally-understood meaning.

The Methods and Examples which follow are intended to illustrate but not limit the invention. In the Methods and Examples, unless otherwise stated:

concentrations were carried out by rotary evaporation in vacuo;

operations were carried out at ambient temperature, that is in the range 18–26° C. and under a nitrogen atmosphere;

column chromatography (by the flash procedure) was performed on Merck Kieselgel silica (Art. 9385);

yields are given for illustrative purposes only and are not necessarily the maximum attainable;

the structure of compounds according to structural diagram I were generally confirmed by conventional NMR and mass spectral techniques, peak multiplicities are shown thus: s, singlet; bs, broad singlet; d, doublet; AB. or dd, doublet of doublets; t, triplet; dt, double of triplets; m, multiplet; bm, broad multiplet; FAB m/s data were obtained using a Platform spectrometer (supplied by Micromass) run in electrospray and, where appropriate, either positive ion data or negative ion data were collected, herein (M+H)+is quoted;

purity of intermediates were was in general assessed by m/s or NMR analysis; and where used the following abbreviations have meanings as follows:

| | |
|---|---|
| DCM | is dichloromethane, |
| DMF | is N,N-dimethylformamide, |
| DMSO | is dimethylsulfoxide, |
| $CDCl_3$ | is deuterated chloroform, |
| FAB | is fast atom bombardment, |
| m/s | is mass spectroscopy or mass spectral, |
| NMR | is Nuclear Magnetic Resonance, |
| NMP | is N-methylpyrrolidinone, and |
| THF | is tetrahydrofuran. |

Biological Methods:

I. N-channel FLIPR (Fluorescent Laser Imaging Plate Reader) Assay.

The methods described herein provide a reliable FLIPR-based readout of the efficacy and potency with which test compounds inhibit calcium flux through the N-type calcium channel expressed in its native form in a human-derived neuroblastoma cell line differentiated chemically to a neuronal phenotype. The degree to which a compound at a particular concentration inhibited the N-channel calcium flux was determined by comparing the amplitude of peak calcium increase in the presence of the compound to a control 80 mM $K^+$ stimulus in wells without compound. Results obtained for this FLIPR assay were validated in two ways:

a) the N-channel specific peptide toxin, conotoxin MVIIA, showed an $IC_{50}$ 3 nM (determined from fit to five-point concentration response analysis), compatible with the known literature value; and b) $IC_{50}$ values were determined certain compounds of the invention ($IC_{50}$ range: 2.37–10.54).

Potency of these same test compounds as inhibitors of the N-type calcium current was also determined by direct electrophysiological measurement either in neuronally differentiated IMR-32 cells, or in freshly-isolated rat superior cervical ganglion neurons. $pIC_{50}$'s yielded by the two methodologies for the compound set were closely comparable (r=0.91; p<0.001).

A. Cell Culture.

An immortalized cell line, IMR32, derived from human neuroblastoma cells obtained from the ATCC (product #CCL-127) was used for all experiments. Cells were grown in T75 flasks containing Eagle's minimum essential medium (MEM) w/Earle's salts and non-essential amino acids without glutamine (Cat.#SLM-034-B, Specialty Media, Philipsburg, N.J.), 10% FBS and 1% glutamine. Cells were grown to ~70–80% confluency (by visual microscopic estimation) before sub-culturing. To maintain a stock culture, cultures were split at a ratio of 1:3–1:4 by creating a cell suspension by trituration, and pipetting a volume of the cell suspension sufficient to yield this final ratio into new flasks containing ~20 mL of fresh media. Sub-culturing was generally performed two times per week. For preparation of 96 well plates (black-walled; Cat # 3603, Costar Co., Cambridge, Mass.), a T75 flask containing cells of desired confluency was brought up to 120 mL volume with media. Cells were then freed by trituration, and the cell suspension was plated into 12–96 well plates to yield final well volume of 100 μL.

B. Cell Differentiation to Neuronal Phenotype.

Cells were induced to differentiate in a differentiation medium consisting of: MEM, 10% FBS, 1% glutamine, 1 μM 2-butyl-cAMP (49.1 mg/100 mL media (Cat. # D-0627, Sigma Corp., St Louis, Mo.), and 2.5 mM bromo-deoxy-uridine (stock: 30.7 mg/10 mL media, 25 mL of above stock/100 mL media; Sigma Cat. # B-9285). To induce differentiation, the cells were treated with differentiation media (by complete medium change) 2 days after an initial plating in 96 well plates. Confluency at this time was ~40%. A complete medium change with freshly prepared differentiating medium was subsequently performed every 2–3 days. Cells were exposed to these differentiation conditions for 6 to 11 days before being used in FLIPR experiments.

C. Standard Experimental Solutions.

Solutions of the following composition (in mM) were used in experiments (Buffers without probenicid purchased from Specialty Media (Buffers A and B: Cat. # BSS053A; Buffers C & D: Cat. # BSS056A).

Buffer A (first wash buffer): Krebs-Ringer-HEPES (KRH) buffer: NaCl: 125, KCl: 5, $MgSO_4$: 1.2, $KH_2PO_4$: 1.2, $CaCl_2$ $2H_2O$: 2, Glucose: 6, HEPES: 25, pH: 7.4 (pH adjusted with NaOH)

Buffer B (dye loading buffer): KRH buffer with 2.5 μM probenicid: same as buffer A, but probenicid added to final concentration of 2.5 μM. Probenecid (Cat. # P-8761, Sigma Chemical Co., St. Louis, Mo.) made as a stock solution at 250 mM.

Buffer C (dye washout buffer): KRH buffer with 0 mM $K^+$ and 2.5 probenicid: NaCl: 130, $MgSO_4$: 1.2, $NaH_2PO_4$: 1.2, $CaCl_2$ $2H_2O$: 2, Glucose: 6, HEPES: 25, pH: 7.4 (pH adjusted with NaOH).

Buffer D (compound dilution buffer): Buffer C with 0.1% w/v bovine serum albumin (BSA; Sigma).

D. Pharmacological Standards and Compounds.

The following solutions were used to obtain the data disclosed herein.

Nitrendipine: (RBI Chemicals, Natick, Mass.): Stock: 10 mM in DMSO; Pipetting solution: 9 μM; pipette 20 μL into 120 μL volume in well for final well concentration: 1 μM.

w-Conotoxin MVIIA: (Cat. # H-8210; Bachem Inc., Torrance, Calif.): Stock: 1 mM in HPLC grade $H_2O$ with 0.1% BSA; Pipetting solution: 4.5 μM; pipette 20 μl into 140 μl volume in well for final well concentration: 1 μM.

Test compound stock and solution preparation: Compounds prepared daily as stocks at 10 mM in 100% DMSO; Pipetting solution: 45 μM or serial dilutions thereof; pipette 20 μL into 140 μL volume in well for final well concentration: 1 μM or 10-fold dilutions thereof.

High potassium (depolarization) solution: Buffer C with 240 mM $K^+$ added; pipette 80 μL into 160 μL volume in well for final well concentration of 80 mM $K^+$.

E. Cell Loading with Fluorescent Dyes.

Fluorescent dye solution preparation: A calcium indicator dye, Fluo-4 acetylmethylester (Fluo 4-AM; Cat. # F-124201; Molecular Probes, Eugene, Oreg.) was used to measure changes in intracellular free calcium with FLIPR-1 mM Fluo-4 μM stock solution was made by dissolution in DMSO. This stock was then diluted to 4.6 μM with Buffer B (Fluo-4 μM working solution).

Cell loading procedure: Plates containing cells were washed with Buffer A using an automated cell washer (Model #: 5161552, Labsystems Oy, Helsinki, Finland) with controls set to the following parameters: cell height: C/D; cell pulse: 4/5, washes: 3; volume: 5; DRY position setting. These settings resulted in a 70 μL residual depth of buffer over cells in each well. 100 μL of the Fluo-4 μM working solution was then added to each well resulting in a final Fluo-4 μM concentration of 2.7 μM Cells were incubated in this solution at 37° C. for 1–1.5 h. Cells were then washed with Buffer C five times using the cell washer with parameters the same as the pre-loading washes above with the exceptions of: washes: 5; WET position setting. A final wash was then conducted by changing the parameters as follows: washes: 1; volume: 2. This resulted in a final well volume of 120 μL. Cells were allowed to equilibrate under this condition for 10 min, and then used in the FLIPR protocol.

F. FLIPR Protocol

Instrumentation: Real time changes in intracellular free calcium in response to potassium-induced depolarization in the absence or presence of putative N-channel inhibitors were measured by either a FLIPR I or FLIPR II (configured for 96-well format) instrument (Molecular Devices, Sunnyvale, Calif.). Identical settings and protocols were used with each instrument, and results obtained from the two instruments were indistinguishable for a set of standard benchmark compounds.

FLIPR hardware settings: Laser power was set to about 0.3 watts. Excitation wavelength was set to a 488 nm peak, and the emission wavelength to 540 nm. Camera aperture was set to 2. All experiments were conducted at room temperature (20–22° C.).

Plate layout—reference signals: Certain wells on each plate were allocated to standards to determine minimum and maximum specific fluorescent signal against which inhibitory effects of compounds were normalized. The reference standards were distributed at plate locations including edge and interior wells Maximum signal (N-channel+non-specific): 12 wells were incubated in nitrendipine (1 μM) solution and 80 M $K^+$ added to determine maximal $Ca^{2+}$ increase mediated by N-channels+non-specific (non-L-, non-N-channel mediated fluorescence increase). The coefficient of variation amongst these wells for the $K^+$-evoked peak increase in fluorescence units was typically less than 12%.

Minimum signal (non-specific): 6 wells were incubated in nitrendipine (1 μM)+w-conotoxin MVIIA and 80 mM $K^+$ added to determine background $Ca^{2+}$ with all N-channels pharmacologically occluded. The peak non-specific signal component was typically less than 15% of the maximum signal peak amplitude.

N-channel reference small molecule: A compound that had been characterized extensively with respect to N-channel inhibitory activity in both FLIPR and patch clamp electrophysiology was included on each plate in triplicate at 1 μM (near $IC_{50}$) to establish a reference point.

Test compounds: 5 test compounds were evaluated for potency on each plate. Each compound was tested at 5 increasing concentrations spanning half-log units and typically reaching a maximal concentration of 10 μM. Each concentration was tested in triplicate wells.

Protocol structure: The FLIPR protocol was configured as three solution addition/sampling sequences (see below). Conotoxin (1 μM final conc.) was added to appropriate wells prior to placing the plate in the FLIPR instrument. Wells initially contained a total solution volume of 100 μl, and after all three solution additions contained 240 μl. The active mixing (by the pipette) option was not used in any sequence.

Nitrendipine addition sequence: 28 s total duration with fluorescence signal sampling at 1 Hz for 2 s, followed by addition of 20 μL nitrendipine standard solution at 10 μL/s, followed by sampling at 0.5 Hz for 24 s.

Test compound addition sequence: 64 s total duration with sampling at 0.5 Hz for 4 sec, test solution addition of 40 μL at 20 μL/s, followed by sampling at 0.2 Hz for 60 S.

Compound incubation, cell depolarization and calcium readout sequence: 1024 s total duration with sampling at 0.0167 Hz for 840 s, followed by solution addition 80 μL of high K$^+$ (depolarization) solution, followed by sampling at 1 Hz for 180 sec. This final 180 sec sampling interval thus represented the epoch where the peak increase in intracellular calcium due to flux through activated N-channels occurred.

G. Data Analysis

FLIPR software: Prior to export, the data was normalized within the FLIPR software module for two effects.

Baseline correction: The baseline was corrected by "zeroing" at sample # 57 (immediately prior to KCl addition). This normalization served to correct the y axis offset of the fluorescent trace from each well so that all traces had a common point just prior to onset of the relevant evoked fluorescent increase.

Spatial uniformity correction factor: The data was normalized by a procedure which calculates a mean over the plate of fluorescent units from the first sample, and then multiplies the data from each well by a scalar that adjusts the value of the first sample to this average value, thus normalizing for differences in absolute baseline fluorescence amongst the wells caused by differences in cell densities or dye loading.

External software: Data were exported from FLIPR into Excel as "*.squ" extension files. Following export, operations were performed in Excel to calculate the maximal peak amplitude (relative to the zeroed baseline) of the fluorescence increase following potassium addition in each well. Measurements from wells where an test compound was added were then normalized as a percentage between the mean amplitudes from the reference wells providing the maximum (100%) and non-specific (0%) signal components, as described above. The resulting percent inhibition by test compounds was considered to reflect inhibition of calcium flux at the N-type channel.

II. L-channel FLIPR Assay.

The methods described below provided a reliable FLIPR-based readout of the efficacy and potency with which test compounds inhibited calcium flux through the L-type calcium channel expressed natively in a human-derived neuroblastoma cell line, SK—N—SH. The degree to which a given compound concentration inhibited the L-channel was determined by comparing the amplitude of peak calcium increase to an 80 mM K$^+$ stimulus in the test well to the peak increase in wells without compound The assay was validated by obtaining 5-point concentration-response curves and thereby determining IC$_{50}$ values for the reference L-channel blockers, nitrendipine (30 nM), nifedipine and verapamil. These values were compatible with the known literature values for these agents to block Ca$^{2+}$ flux through the L-channel.

A. Cell Culture:

An immortalized cell line, SK—N—SH, derived from human neuroblastoma cells (ATCC product # HTB-11) was used for all experiments. Cells were grown in T75 flasks containing Eagle's minimum essential medium (MEM) w/Earle's salts, with 0.1 mM non-essential amino acids, 1.0 mM Na pyruvate and 10% fetal bovine serum (FBS; Cat. # SLM-034-B, Specialty Media). Cells were grown to 100% confluency (by visual microscopic estimation) before sub-culture. Cells were sub-cultured at a ratio of 1:3 by first rinsing with 3 mL PBS, replacing the PBS with PBS containing 0.25% trypsin until the cells detached from the surface. 1 mL of the resulting suspension was then added to a new flask containing 10 mL fresh media. Cells were then incubated (37° C., 5% CO$_2$), and media was exchanged about 3 days after subculturing.

B. Preparation of Cells for Experiments:

Cells used for experiments were at the 100% confluency growth stage. Each flask provided enough cells for three 96-well plates. Cells were detached from the flask by addition of 0.25% trypsin, as described for the sub-culturing protocol. Once detached, 7 mL fresh media was added to the flask, and the solution triturated gently. An additional 20 mL media was then added, and 100 μL of this final cell suspension was then added to each well of a 96-well plate. Before use in experiments the plates were incubated at 37° C. in 5% CO$_2$ until cells reached 100% confluence (1–2 days).

C. Experimental Procedures:

The composition of solutions, hardware settings, plate layout, structure of the FLIPR protocol, and analytical settings and procedures were identical to those described herein for the N-channel assays with the following differences as regards Plate layout and reference signals.

Maximum signal (L-channel+non-specific): 12 wells received 20 μL buffer addition only (no nitrendipine) in the first solution addition sequence to define the maximal K$^+$-evoked Ca$^{2+}$ increase mediated by L-channels+non-specific (non-L-channel mediated fluorescence increase). The coefficient of variation amongst these wells for the K$^+$-evoked peak increase in fluorescence units was typically less than 12%.

Minimum signal (non-specific): 6 wells were incubated in nitrendipine (1 μM), followed by 80 mM K$^+$ added to determine background Ca$^{2+}$ with all L-channels pharmacologically occluded. The peak non-specific signal component was typically less than 15% of the maximum signal peak amplitude.

L-channel reference small molecule: Nitrendipine was included in triplicate wells on each plate at 30 nM (near IC$_{50}$) for a reference readout.

III. N-Channel Patch Clamp Electrophysiology.

Conventional whole cell recording techniques were used to directly measure the ability of test compounds to inhibit Ca$^{2+}$ current through N-type calcium channels. N-type current were recorded from both neuronally differentiated IMR-32 cells, and native neurons freshly dissociated from superior cervical ganglia of early postnatal rats. Each day, currents in both cell types were confirmed as N-currents showing that greater than 90% of the total inward current during depolarizing steps was blocked by a supramaximal concentration (3 mM) of w-conotoxin MVIIA. Additionally, the potency of w-conotoxin MVIIA was periodically determined to be about 3 nM (IC$_{50}$), a value consistent with that reported in the literature. Results for a subset of compounds tested in both cell types did not differ significantly, thus data are considered as one data set unless otherwise specified.

A. IMR-32 Cell Culture and Differentiation:

IMR32 cells were cultured and neuronally differentiated using procedures identical to those described for the FLIPR N-channel assay except that for differentiation cells were plated in 35 mm plexiglass culture dishes, rather than 96-well plates.

B. Dissociation of Rat Superior Cervical Ganglion (SCG) Neurons:

7–10 day old rat pups were euthanized in a chamber containing a high CO$_2$ atmosphere. Immediately, SCG were surgically isolated, removed and placed in ice cold Hanks balance salt solution (HBSS). SCG's were desheathed, cut open and placed in a solution of HBSS containing 20 U/mL papain (37° C.) for 15 min. The papain solution was then exchanged for HBSS (37° C.) containing 16 mg/mL dispase and 400 U/mL collagenase for 40 min with gentle trituration of tissue every 15 min. Cells were then recovered by centrifugation and stored in L-15 medium at 4° C. for use on the same day. For recording, a drop of cell containing solution was placed on a poly-L-lysine coated 35 mm plexiglass culture dish, and cells allowed to adhere for several minutes.

C. Electrophysiological Procedures:

Solutions: Recording solutions were adapted from those described by Thompson and Wong (1991) *J. Physiol.*, 439: 671–689. Solutions were stored as aliquots for not more than one month (intracellular, −20° C., extracellular, 4° C.) before experiments. The pipette (intracellular) solution contained (in mM): TRIS, 130; CsBAPTA, 10; HEPES, 10; $Mg^{2+}ATP$, 5; pH to 7.3 with methanesulphonic acid; osmolality ~315 mOsm. Extracellular solution contained (in mM): TRIS 120; CsCl, 5; HEPES, 10; $Mg^{2+}Cl$, 1; $Ba^{2+}Cl$, 5, glucose, 25; tetraethylammonium chloride, 15; tetrodotoxin, 200 (added at time of experiment); pH to 7.4 with methanesulphonic acid; osmolality ~320 mOsm.

Whole cell recording and analysis: The whole-cell voltage clamp configuration of the patch clamp technique as described by Hamill et al. (1981) *Pflügers Arch.* 391: 85–100, was employed to isolate voltage-dependent calcium currents. Culture dishes containing cells were placed in a chamber on the stage of an inverted microscope. All experiments were conducted at room temperature (20–22° C.). Patch pipettes were fabricated from thin-wall glass (1.5 mm OD, 1.12 mm ID; World Precision Instruments, New Haven, Conn.) on the Brown-Flaming P-86 puller (DC resistance: 3–6 MΩ; Sutter Instr. Co., Novato, Calif.). An Axopatch 1B amplifier (Axon Instruments, Foster City, Calif.) was used to obtain current signals and this was connected to a personal computer by either a TL-1 (Scientific Solutions, Solon, Ohio) or Digidata 1200 (Axon Instr.) interface. The current signal was balanced to zero with the pipette immersed in the bath just prior to forming a seal on the neuron. Seal resistance ranged from 1 to greater than 10 GΩ. Series resistance was usually less than 10 MΩ, and was not compensated electronically. Digitized data acquisition and voltage step protocols were accomplished with pClamp 6.0 software (Axon Instr). Data were low-pass filtered at less than one-half the digital sampling rate prior to digitizing. To record N-type currents for evaluation of inhibitory potency of compounds (steady-state concentration-response analysis), 200 ms voltage steps to +10 mV were delivered at 15 sec intervals from a holding potential of −90 mV. The recorded currents were leak subtracted on-line with a P-4 or P-6 subpulse protocol in the pClamp software. To evaluate open channel block of compounds, 10 ms voltage steps to +10 mV were delivered at varying frequencies from a holding potential of −90 mV without using on-line leak subtraction. These voltage protocols both yielded constant inward current amplitudes over 5–10 minutes of recording. Peak current amplitude was analyzed using the clampfit module of pClamp software. Origin 5.0 software (Microcal Corp, Northampton, Mass.) was used to iteratively fit concentration-response data to a standard Hill function, and to provide graphic displays for current traces and analyzed data.

Drug/compound preparation and delivery: Test compounds were prepared as 10 mM stock solutions in DMSO, and appropriate volumes of these stock solutions dissolved into extracellular buffer to yield the desired concentrations. Solutions containing drugs/compounds were applied focally from any of six linearly arranged glass-lined tubes (200 mm o.d., Hewlett Packard, Wilmington, Del.) positioned ~100 mm from the recorded neuron. Each solution was released from the desired tube by an electronically controlled solenoid valve system (BME Systems, Baltimore, Md.). This system achieved rapid (<100 ms) equilibration of drug solution in the extracellular phase without perturbing the recording characteristics.

Compounds of the invention generally had a binding affinity, expressed as the $IC_{50}$ ($\mu$M), for the N-type calcium channel, as measured by the FLIPR assay, of about 10 $\mu$M or less. For example, the compounds of Examples 4, 66, 74 and 75, respectively have $IC_{50}$'s of 3.57, 2.37, 3.56 and 10.54 $\mu$M.

IV. Formalin Test.

The Formalin test assesses the inhibitory effects of orally administered N-type calcium channel antagonists on formalin-induced nocifensive behaviours in rats. The formalin test is a well established pain test (Dubuisson and Dennis, 1977; Wheeler-Aceto et al., 1996; Coderre et al., 1993). This test consists of two distinct phases of formalin-induced behaviour. The first phase response, occurring between 0 to 5 minutes, is caused by acute nociception to the noxious chemical (formalin) injected into the paw. This is followed by a quiescent period of between 5 to 15 min post injection. A second phase response, occurring after 15 minutes and lasting up to 60 minutes, is caused by sensitisation of the central neurons in the dorsal horn. Central sensitisation augments the noxious afferent input and a stronger pain barrage is transmitted into the brain. Inhibition of the second phase response is indicative of a central mechanism of drug action.

The procedure for the formalin test is as follows: male rats are placed in a plexiglass chamber and observed for 30–45 min. to observe their baseline activity. Multiple groups of animals are pretreated with either vehicle or different doses of a test compound. Animals are dosed with the drug of interest either 40 min., if by the intraperitoneal route, or 90 min., if by the oral route, prior to injection of formalin into a hind paw (under the dorsal skin; 0.05 mL of sterile 5% formalin). The number of paw flinches and licks during first phase (0–5 min.) and second phase (20–35 min.) are scored and recorded. Flinch and lick responses are calculated as percentage of inhibition compared with the mean score of a saline control group. Drug potencies are expressed as the dose which causes 50% of the maximum inhibitory effect ("$ID_{50}$"). Student t-tests are used for statistical analysis to determine the significance of drug effects. Compounds are considered active based on their ability to inhibit the flinch response.

V. Chronic Constrictive Injury Test.

The Chronic Constrictive Injury ("CCI") test or Neuropathic Pain Model assesses neuropathic pain associated with nerve injuries that can arise directly from trauma and compression, or indirectly from diseases ranging from infection to cancer, metabolic conditions, toxins, nutritional deficiencies, immunological dysfunction and musculoskeletal changes. In the CCI model (Bennett and Xie, 1988) a unilateral peripheral neuropathy is produced in rats by partial nerve ligation.

Sprague-Dawley rats (250–350 g) are anesthetized with sodium pentobarbital and the common sciatic nerve is exposed at the level of the mid-thigh by blunt dissection through the biceps femoris. A section of nerve (about 7 mm), proximal to the sciatic trifurcation, is exposed and ligated 4 times with chromic gut suture. The suture is tied with about 1 mm spacing between ligatures. The incision is closed in layers and the animals are allowed to recover. Thermal hyperalgesia is measured using the paw-withdrawal test (Hargreaves et al, 1988). Nerve compression due to the partial nerve ligation causes shorter latencies for paw withdrawal compared to the latency of paw withdrawal of paws of normal or sham operated legs. Animals are habituated on an elevated glass floor. A radiant heat source is aimed at the mid-plantar hindpaw (sciatic nerve territory) through the glass floor with a 20 second cut-off used to prevent injury to the skin. Latencies for the withdrawal reflex in both paws are recorded. Response to test compounds are evaluated at different times following oral administration to determine onset and duration of drug effect. Dose response studies are conducted with multiple groups of CCI rats dosed orally with either vehicle or the test compound for 5 days. Paw withdrawal latencies are measured each day prior to the first daily dose. Data analysis is performed by multiple means comparison (Dunnett's test) and drug potencies are expressed as the dose which causes 50% of the maximum efficacy ("$EC_{50}$").

Chemical Methods:

Method A:

Certain intermediates of exemplary compounds disclosed herein, see Table 1, were prepared in a manner analogous to this method which describes the preparation of the quinoline intermediate, 2-(4-cyclohexylphenyl)-4,6-quinolinediamine, of Example 58.

3-(4-Cyclohexylphenyl)-3-oxo-propionic Acid Ethyl Ester

A 60% oil dispersion of sodium hydride 21.7 g (0.543 moles) was placed in a three neck 2 L round bottom flask equipped with an addition funnel, nitrogen inlet, magnetic stirrer, heating mantle, thermocouple and condenser. To this was added 1 liter of dry hexane. The resulting suspension was then stirred for 15 minutes, stirring stopped and the solids allowed to settle. The clear supernatant containing the hexane and dissolved oil was then removed via cannula. Diethyl carbonate (1 L) was added to the solids and the suspension was heated to 120° C. To this suspension a solution of 100 g (0.494 moles) of 4'-cyclohexyl acetophenone dissolved in 250 mL of diethyl carbonate was cautiously added dropwise, over 40 minutes. As addition proceeded a reaction initiated, hydrogen was evolved and the color changed to tan. After the acetophenone derivative addition was complete, the mixture was heated for 1 additional hour. The reaction was cooled and was poured into a 2 L separatory funnel. The diethyl carbonate layer was recovered, washed twice with 10% acetic acid solution and dried over $MgSO_4$. The diethyl carbonate solution was then filtered and concentrated on a rotary evaporator followed by pumping under high vacuum at 70° C. for 18 hr. Upon cooling over 24 hrs a colorless solid crystallized. The title compound obtained was used without further purification. Yield 133 g (98%). $^1H$ NMR revealed that the b-keto ester product actually exists as a keto-enol tautomer mixture in solution, with the keto form predominant in the solid.

3-(4-Acetylaminophenylamino)-3-(4cyclohexylphenyl)-acrylic acid butyl ester 3-(4-Cyclohexylphenyl)-3-oxo-propionic acid ethyl ester 50.25 g (0.183 moles), 4'-aminoacetanilide 25 g (0.167 moles), 4'-aminoacetanilide hydrochloride salt, 1.55 g (0.008 moles), and 500 mL of dry n-butanol were placed in a 1 liter single neck round bottom flask equipped with a Soxhlet extractor apparatus with condenser, magnetic stirrer and nitrogen inlet. In the Soxhlet thimble (33×118 mm) was placed highly activated 4A sieves (1.7–2.4 mm beads). The sieves were activated immediately before use under high vacuum with heating (400° C. for 30 min). The mixture was then brought to reflux such that the butanol azeotropically removed water, so as to drive the equilibrium reaction, and the water was removed from the butanol by the sieves before being returned to the reaction pot. The reaction was allowed to continue for 48 hrs. The charge of sieves was replaced after the first 24 hrs. Transesterification to the butyl ester along with removal of ethanol occurred concomitantly with enamine formation. After 48 hrs the reaction pot was cooled, placed in a −40° C. freezer and crystals were-allowed to form for 24 hrs. Crystals were collected by vacuum filtration and solids washed with cold ethanol. The product was then dried in a vacuum oven to give 73.8 g (98%) of the desired enamine.

N-[2-(4-Cyclohexylphenyl)-4-hydroxy-quinolin-6-yl]-acetamide 1.2 L of Dowtherm A was charged into a 2 L three neck round bottom flask equipped with a condenser, magnetic stirrer, thermocouple, heating mantle with a variable voltage controller, and a nitrogen inlet. The solvent was heated to 250° C. and 3-(4-acetylaminophenylamino)-3-(4-cyclohexylphenyl)-acrylic acid butyl ester 48 g (0.11 moles) was cautiously added in small portions. As portions were added gas was evolved and foaming occurred. Crystals of product began to form and adhere to the sides of the vessel. After all material had been added heating of the mixture was continued for 1 hour. The mixture was then cooled to room temperature and hexane added. A solid product was collected by vacuum filtration and washed with hexane. After drying in a vacuum oven, 35.7 g (90%) of product was recovered.

N-[2-(4-Cyclohexylphenyl)-4-methoxy-quinolin-6-yl]-acetamide

N-[2-(4-Cyclohexylphenyl)-4-hydroxy-quinolin-6-yl]-acetamide 35.7 g (0.099 moles) was placed in a 500 mL three neck round bottom flask equipped with a condenser, magnetic stirrer and nitrogen inlet with 250 mL of toluene. The material was suspended by stirring and 20.6 mL (0.21 moles) of dimethyl sulfate was added. The suspension was then heated with a silicone oil heating bath, to gentle reflux for 18 hr. After thwas time the reaction was allowed to cool and hexane was added. Solids were collected by vacuum filtration and washed with hexane. After drying, the solids were suspended in a 2 L Erlenmeyer flask with 1 L of 5% sodium hydroxide solution. The suspension was vigorously stirred and heated to 70° C. for 30 min. This converted the salt form of the material to the free base and removed some impurities. After cooling the solids were collected by vacuum filtration and washed with water. The product was dried in a vacuum oven to give 35.8 g (96%) of material, which contained about 30% of side products, with the N-methylated material constituting the major impurity. The material was used without further purification.

N-[4-Amino-2-(4-cyclohexylphenyl)-quinolin-6-yl]-acetamide

N-[2-(4-Cyclohexylphenyl)-4-methoxy-quinolin-6-yl]-acetamide (35 g) was placed in a 500 mL three neck round bottom flask equipped with a mechanical stirrer and condenser, nitrogen inlet and gas outlet with 250 g of ammonium acetate. The stirred solid suspension was then heated to 115° C. Ammonia was evolved and the material fused and dissolved in the acetic acid that formed over time. The temperature was slowly raised to 140° C. over 1 hr. Caution was used to ensure that the condenser and gas outlet remain clear of solid ammonium acetate, which collects on cool surfaces from sublimation of excess ammonium acetate. After 4 hours of heating, the reaction was cooled and poured into 1 L of water. The pH was then adjusted to 9.5 by the slow addition of a concentrated NaOH solution with application of ice cooling. Ethyl acetate was then added and the mixture filtered. Solid impurities, some of which are N-methylated side products from the previous step, were removed and the liquid filtrate was poured into a 2 L separatory funnel. The ethyl acetate layer was recovered, washed twice with 5% NaOH solution and then dried over $Na_2SO4$. After filtration, the solvent was evaporated to give 22 g (60%) of a solid which consisted mainly of the desired product with about 20% of the N6-deacetylated material, 2-(4-cyclohexylphenyl)-4,6-quinolinediamine. The material was used without further purification.

2-(4-Cyclohexylphenyl)-4,6-quinolinediamine

N-[4-Amino-2-(4-cyclohexylphenyl)-quinolin-6-yl]-acetamide (22 g) was placed in a 1 L flask to which 500 mL of 6 N HCl was added and the mixture heated with stirring to 95° C. for 18 hrs. After this time, the solution was cooled in ice and was then cautiously neutralized with concentrated NaOH solution, followed by adjustment to pH 9.5. The solution was then poured into a 2 L separatory funnel and extracted with ethyl acetate. The organic layer was then dried over $Na_2SO_4$, filtered and concentrated to give 17 g of the desired product. Repeated crystallization using methanol, methylene chloride and hexane provided 9.0 g (41%) of the pure title compound.

Method B:

Certain intermediates of exemplary compounds disclosed herein, see Table 1, were prepared in a manner analogous to this method which describes the preparation of the quinoline intermediate, 2-(3-fluorophenyl)-4,6-quinolinediamine, of Example 99.

3-(3-Fluorophenyl)-3-oxo-propionic acid ethyl ester

This compound was prepared from m-fluoro acetophenone, in a manner analogous to the preparation of 3-(4cyclohexylphenyl)-3-oxo-propionic acid ethyl ester (Method A), except that the product was purified by vacuum distillation (bp 114–117° C. at 0.8–0.9 mmHg) in 91% yield.

3-(4-Nitrophenylamino)-3-(3-fluorophenyl)-acrylic acid butyl ester

4-Nitroaniline 63.0 grams (0.456 moles), 4-nitro-aniline hydrochloride 4.0 grams (0.023 moles) 3-(3-fluorophenyl)-3-oxo-propionic acid ethyl ester 106.3 grams (0.506 moles) and were placed in a dry 2 L round bottom flask. To the mixture was added 1.3 L of n-butanol and the flask fitted with a Soxhlet extractor (cup volume of 0.3 L), condenser and nitrogen inlet. Dry, activated 4 Å sieves (200 grams) were placed in the extractor cup and the reaction mixture heated to reflux temperature of 118° C. under nitrogen and maintained at that temperature for 90 hours. The reaction mixture was decanted while hot from a small amount of solids and chilled to −15° C. for 48 hours Crystalline solids were collected by vacuum filtration. The crystals were washed with 0.2 L of cold ethanol and two 0.2 L portions of hexanes and vacuum dried at 50° C. overnight to yield 35.8 grams (20.8% yield) of the title compound.

The mother liquors from the foregoing reaction were concentrated, diluted with 1.0 L of toluene and the toluene removed in vacuo; this process was repeated two times. The liquors were then diluted in 1.0 L of n-butanol and 1.75 grams (10.0 mmol) of 4-nitro-aniline hydrochloride added; the flask was fitted with a Soxhlet extractor as previously described and the cup charged with a fresh 200 grams of sieves. The mixture was placed under nitrogen and brought to reflux temperature for 90 hours. The mixture was then cooled and then reduced to a final volume of 0.6 L in vacuo. The solution was then seeded with crystalline 3-(4-nitrophenylamino)-3-(3-fluorophenyl)-acrylic acid butyl ester and let stand at −15° C. for 48 hours. Crystals were collected as described before and 64.3 grams were obtained after drying. Analysis showed this material to contain 4-nitro-aniline and it was subjected to flash chromatography. The product was dissolved in 0.5 L of 1:1 methylene chloride to hexane and applied to a column of 3.0 L of silica wet-packed in 1:1 methylene chloride to hexane. The column was eluted with 4.0 L of 1:1 methylene chloride to hexane; 9.0 L of 2:1 methylene chloride to hexane; and 2.0 L of methylene chloride. Fractions of 0.5 L were collected and those containing the desired product were combined to yield 41.7 grams (24.3%) of a bright yellow solid. The combined yield was 45.1%.

2-(3-Fluorophenyl)-6-nitro-quinolin-4-ol

Dowtherm A, 0.75 L, was placed in a 3 L three-neck flask, equipped with mechanical stirrer, Claisen adapter holding a thermocouple probe and reflux condenser with nitrogen inlet and heated to 250° C. To this was cautiously added in small portions 77.0 grams (0.215 moles) of 3-(4-nitrophenylamino)-3-(3-fluorophenyl)-acrylic acid butyl ester over the course of 0.25 hours. The mixture was maintained at 250° C. for 1.5 hours and then allowed to cool to 90° C. over the course of 2 hours. The mixture was treated with 1.0 L of hexanes, and allowed to cool to room temperature while string overnight. The tan solids were collected by suction filtration and washed with three 0.15 L portion of hexanes. The solids were dried under vacuum at 50° C. overnight to yield 58.63 grams (96.0%) of the title compound.

6-Nitro-4-chloro-2-(3-fluorophenyl-quinoline

6-Nitro-2-(3-fluorophenyl)-quinolin-4-ol 5.2 g (16.3 mmoles) was placed in a 500 mL three neck round bottom flask equipped with a condenser, magnetic stirrer and nitrogen inlet. To this was added 15.2 mL (25.0 g, 163 mmoles, 10 eqiv.) of phosphorus oxychloride with stirring. The mixture was then heated to 110° C. for 4 hr. At the end of this time the reaction was cooled to room temperature and water was cautiously added dropwise until all of the $POCl_3$ was consumed. A material crystallized from the water and the solids were collected by filtration. The solids were then washed with water and then placed in a 250 mL Erlenmeyer and triturated with water. After collection by filtration, washing with water, and drying in a vacuum oven, 4.6 g (84%) of the title compound was obtained.

6-Nitro-4-azido-2-(3-fluorophenyl)-quinoline

6-Nitro-4-chloro-2-(3-fluorophenyl)-quinoline 3.2 g (9.50 mmoles) was placed in a 250 mL three neck round bottom flask equipped with a condenser, magnetic stirrer, silicone oil heating bath, nitrogen inlet and gas outlet. To this was added 75 mL of N-methyl pyrrolidinone then 6.0 g (95 mmoles, 10 equiv.) of sodium azide. The mixture was stirred and warmed to 60° C. for 18 hr. After this time the mixture was cooled, poured into a 1 L separatory funnel containing 500 mL water and 250 mL of ethyl acetate. The pH was adjusted to 9.0 and the layers separated. The aqueous layer was extracted twice with 100 mL of ethyl acetate, the organic layers combined, dried over $Na_2SO_4$, filtered and concentrated to yield a product, which was carried to the next step without further purification.

2-(3-Fluorophenyl)-4,6-quinolinediamine

6-Nitro-4-azido-2-(3-fluorophenyl)-quinoline was placed in a 500 mL three neck flask equipped with a condenser, magnetic stirrer, nitrogen inlet gas outlet and a silicone oil heating bath and suspended in 250 mL of ethyl acetate and 50 mL of ethanol. The mixture was stirred, heated to reflux, 20 g (89 mmoles, 6 equiv.) of stannous chloride dihydrate cautiously added portionwise over 40 min, and the mixture was heated for an additional 2 hr. At the end of this time, the mixture was cooled and poured into 500 mL of water. The pH was cautiously adjusted to 9.0 and the solution filtered. Solids were washed with 100 mL of ethyl acetate, the filtrates combined and the aqueous layer twice extracted with 200 mL of ethyl acetate. The organic layers were combined dried over $Na_2SO_4$, filtered and concentrated. The product was chromatographed on a silica gel column, using 10% methanol in ethyl acetate as eluent, and was then recrystallized from methylene chloride and hexane to give 3.6 g (88%) of the title compound.

Method C:

An intermediate, 3-(methyl-propoxy)-3-oxo-propionic acid ethyl ester, used for the preparation of Exemplary compound 21 disclosed herein, see Table 1, was prepared by the following method.

3-(methyl-propoxy)-3-oxo-propionic Acid Ethyl Ester

A sodium hydride dispersion in mineral oil, 160.0 grams (60%, 4.0 moles) was placed in a 12 L round bottom flask equipped with mechanical stirrer, thermometer, addition funnel and nitrogen inlet. The flask was cooled with an ice bath and 3.5 L of dry THF added with sting, while maintaining the temperature below 20° C. To the suspension of stirred sodium hydride was added 376.4 grams (4.0 moles) of iso-butanol dissolved in 0.3 L of THF. The addition was carried out over about 2 hrs. at such a rate so as to maintain the temperature below 10° C. The mixture was then allowed to warm to room temperature and stired for 1 hour. To the re-cooled solution, over the course of 1 hour, was added 418 grams (2.0 moles) of ethyl 4-bromoacetoacetate (A. Svendsen, and P. M. Boll, *Tetrahedron* 1973 29, 4251–4258) dissolved in 0.3 L of THF. The rate of addition was controlled so as to keep the temperature below 10° C. The ice bath was removed and the brown slurry stirred overnight at room temperature. The reaction was quenched by pouring into 2.2 L of 1.0 N hydrochloric acid and the phases separated. The aqueous phase was extracted with 0.5 L of diethyl ether; the combined organic phase washed with 1.0 L of saturated brine and dried over $MgSO_4$. After filtering and removal of solvent 830 g of a red-brown oil was obtained. The product was dissolved in 0.4 L of hexane and applied to a column of 8.0 L of silica wet-packed in hexane. The column was eluted with 4.0 L of hexane; 8.0 L of 3:1 hexane to diethyl ether and 12.0 L of 2:1 hexane to diethyl ether. The second fraction, 459.3 gram, was reapplied to a column of 4.0 L of silica wet-packed in hexane. The column was eluted with 3.0 L of 95:5 hexane to diethyl ether; 2.0 L of 9:1 hexane to diethyl ether; 2.0 L of 4:1 hexane to diethyl ether and 12.0 L of 3:1 hexane to diethyl ether. The major fraction was bulb-to-bulb distilled using a Kugelrohr apparatus and an oven temperature of 40–45° C. at <1.0 torr. The desired product was obtained as an oil, 145.9 gram (33%).

Method D:

An intermediate, N-[2-(3-fluorophenyl)-6-amino-4-quinolinyl]-N,N-dimethylamine, used for the preparation of Exemplary compound 124 disclosed herein, see Table 1, was prepared by the following method.

3-(3-Fluorophenyl)-3-oxo-propionic acid ethyl ester:

A 60%-in-oil dispersion of sodium hydride, 21.7 g (0.543 moles), was placed in a three-neck 2 L round-bottom flask equipped with an addition funnel, nitrogen inlet, magnetic stirrer, heating mantle, thermocouple and condenser with dry hexane (1 L). The resulting suspension was stirred for 15 minutes, stirring was halted and the solids were allowed to settle. The clear supernatant containing the hexane and dissolved oil was then removed via a cannula. Diethyl carbonate (1 L) was added and the suspension was heated to 120° C. To this suspension was cautiously added dropwise, over 40 minutes, a solution of 100 g (0.494 moles) of m-fluoro acetophenone dissolved in 250 mL of diethyl carbonate. As addition proceeded a reaction initiated, hydrogen was evolved and the color changed to tan. After the acetophenone derivative addition was complete, the reaction was heated for 1 additional hour. The reaction mixture was cooled and was poured into a 2 L separatory funnel. The diethyl carbonate layer was twice washed with 10% acetic acid solution and then purified by vacuum distillation (bp 114–117° C. at 0.8–0.9 mm Hg) in 91% yield.

3-(4-Nitrophenylamino)-3-(3-fluorophenyl)-acrylic Acid Butyl Ester:

3-(3-Fluorophenyl)-3-oxo-propionic acid ethyl ester, 106.3 grams (0.506 moles), 4-nitro-aniline, 63.0 grams (0.456 moles), and 4-nitro-aniline hydrochloride 4.0 grams (0.023 moles) were placed in a dry 2 L round-bottom flask. To the mixture was added 1.3 L of n-butanol, the flask was fitted with a Soxhlet extractor (cup volume of 0.3 L), condenser and nitrogen inlet. Dry, activated 4 Å sieves (200 grams) were placed in the extractor cup and the reaction mixture heated to reflux at 118° C. under nitrogen and maintained at that temperature for 90 hours. The reaction mixture was decanted while hot from a small amount of solids and chilled to −15° C. for 48 hours Crystalline solids were collected by vacuum filtration. The crystals were washed with 0.2 L of cold ethanol and two 0.2 L portions of hexanes and vacuum dried at 50° C. overnight to yield 35.8 grams (20.8% yield) of the title compound.

The mother liquors from the foregoing reaction were concentrated, diluted with 1.0 L of toluene and the toluene removed in vacuo; this process was repeated two times. The liquors were then diluted in 1.0 L of n-butanol and another 1.75 grams (10.0 mmol) of 4-nitro-aniline hydrochloride added; the flask was fitted with a Soxhlet extractor as before and the cup charged with a fresh 200 grams of sieves. The mixture was placed under nitrogen and brought to reflux temperature for 90 hours. The reaction was cooled and then reduced to a final volume of 0.6 L in vacuo. The solution was then seeded with crystalline 3-(4-nitro-phenylamino)-3-(3-fluoro-phenyl)-acrylic acid butyl ester and let stand at −15° C. for 48 hours. The crystals were collected as before; 64.3 grams obtained after drying. Analysis showed this material to be contaminated with 4-nitro-aniline and it was purified by flash chromatography. The product was dissolved in 0.5 L of 1:1 methylene chloride to hexane and applied to a column of 3.0 L of silica wet-packed in 1:1 methylene chloride to hexane. The column was eluted with 4.0 L of 1:1 methylene chloride to hexane; 9.0 L of 2:1 methylene chloride to hexane; and 2.0 L of methylene chloride. Fractions of 0.5 L were collected and those containing the desired product combined to yield 41.7 grams (24.3%) of bright yellow solid. The combined yield was 45.1%.

2-(3-Fluoro-phenyl)-6-nitro-quinolin-4-ol:

Dowtherm A, 0.75 L, was placed in a 3 L three-neck flask, equipped with mechanical stirrer, Claisen adapter holding a thermocouple probe and reflux condenser with nitrogen inlet and heated to 250° C. To this was cautiously added in small portions 77.0 grams (0.215 moles) of 3-(4-nitrophenylamino)-3-(3-fluorophenyl) acrylic acid butyl ester over the course of 0.25 hours. The mixture was maintained at 250° C. for 1.5 hours and then allowed to cool to 90° C. over the course of 2 hours. The mixture was treated with 1.0 L of hexanes, and allowed to cool to room temperature while stirring overnight. The tan solids were collected by suction filtration and washed with three 0.15 L portions of hexanes. The solids were dried under vacuum at 50° C. overnight to yield 58.63 g (96.0%) of the title compound.

6-Nitro-4-chloro-2-(3-fluoro-phenyl)-quinoline:

6-Nitro-2-(3-fluoro-phenyl)-quinolin-4-ol, 5.2 g (16.3 mmoles), was placed in a 500 mL three-neck round-bottom flask equipped with a condenser, magnetic stirrer and nitrogen inlet. To this was added 15.2 mL (25.0 g, 163 mmoles, 10 equiv.) of phosphorus oxychloride with stirring. The mixture was heated to 110° C. for 4 hr. At the end of this time the reaction was cooled to room temperature and water was cautiously added dropwise until all of the POCl$_3$ was consumed. The product crystallised from the water and solids were collected by filtration. The solids were washed with water, placed in a 250 mL Erlenmeyer and triturated with water. After collection by filtration, washing with water, and drying in a vacuum oven, 4.6 g (84%) of the product was obtained.

N-[6-Nitro-2-(3-fluorophenyl)-4-quinolinyl]-N,N-dimethylamine:

6-Nitro-4-chloro-2-(3-fluoro-phenyl)-quinoline, 20 g (59.4 mmoles), was placed in a 500 mL three-neck round-bottom flask equipped with magnetic stirrer, nitrogen inlet, gas outlet, condenser and heating bath. The material was dissolved in 150 mL of N-methyl pyrrolidinone, stirred and 250 mL of a 40% aq. solution of dimethylamine was added. The mixture was then warmed to 60° C. for 48 hrs. At the end of this time the reaction was cooled, poured into 3 L of water in a 4 L Erlenmeyer flask and the mixture stirred until solids formed. The solids were collected by vacuum filtration and dried in a vacuum oven. The product was recrystallised from ethanol in a −20° C. freezer to give 19.6 g (95%) yield of the desired product.

N-[2-(3-Fluorophenyl)-6-amino-quinolinyl]-N,N-dimethylamine

N-[6-Nitro-2-(3-fluorophenyl)-4-quinolinyl]-N,N-dimethylamine with 150 mg of a catalyst consisting of 5% palladium on calcium carbonate support was placed in a 500 mL Parr shaker bottle. To this was added 150 mL of ethanol, followed by application of a 50 psi hydrogen atmosphere. The mixture was shaken for 18 hr and the hydrogen atmosphere then replaced by nitrogen. The catalyst was removed by filtration and the solution concentrated. The residue was taken up in ethyl acetate, washed with 5% sodium hydroxide solution, the organic layer was dried over Na$_2$SO$_4$, filtered and then concentrated. The extract was recrystallized from methylene chloride and hexane to give 2.8 g (77%) of the title compound.

N-[2-(3-fluorophenyl)-6-amino-4-quinolinyl]-N,N-dimethylamine was also prepared by reduction of the 6-nitro group using stannous chloride as in Method B.

Method E:

Intermediates used in the synthesis of Exemplary compounds disclosed herein were made in a manner analogous to the following procedure.

Hydroxy-Pyrimidines

Into an oven-dried three neck round bottom, equipped with reflux condenser and nitrogen inlet, and two addition funnels with stoppers, were added oven-activated 5 Å molecular sieves under a stream of dry nitrogen. Sodium hydride (95%) 3.03 grams (0.126 mole) was added to the room temperature flask followed by 40 mL of dry DMF. Stirring was initiated to achieve a suspension of the solids. A solution of guanidine hydrochloride, 11.9 grams (0.125 mole) dissolved in 40 mL of dry DMF was added dropwise via addition funnel over 0.25 hours and stirring was continued for 0.5 hours at room temperature. 3-(4-Fluorophenyl)-3-oxo-propionic ethyl ester, 26.28 grams (0.125 mole) was dissolved in 75 mL of dry DMF and added to the reaction flask via dropper funnel over 0.25 hours. The mixture was then heated at reflux overnight. The mixture was filtered hot and concentrated to afford a heterogeneous mixture. Water, 100 mL, was added and a solid that formed was filtered off and dried. The solid was recrystallized from methanol to afford 4-hydroxy-6-(4-fluorophenyl)pyrimidin-2-amine (51% yield). Hydroxy-pyrimidine compounds were used in the procedure of Method G.

Method F:

Chloro-pyrimidines

Dry 4-hydroxy-6-(4-fluorophenyl)pyrimidin-2-amine, 24 gm (0.117 mole), was weighed directly into a 250 mL round bottom flask. Under a stream of dry nitrogen 24.1 grams (0.117 mole) of phosphorus pentachloride was added followed by 100 mL of phosphoryloxychloride. The mixture was maintained at reflux overnight, after which time the liquid phase was removed by evaporation and ice chunks were added to the reaction flask. Saturated sodium carbonate was then added until the stirred mixture was basic and a solid precipitate formed. The solid, 4-chloro-6-(4-fluorophenyl)pyrimidin-2-amine, was filtered off and dried, 14.4 grams (55%). Chloro-pyrimidine compounds were used in the procedure of Method H.

Method G:

Exemplary compounds disclosed herein, see Table 1, were prepared in a manner analogous to the following method which describes the preparation of N6-[2-amino-6-(4-butylphenyl)pyrimidin-4-yl]-2-(4-fluorophenyl)-quinoline-4,6-diamine, the compound of Example 111 from triflate imtermediates.

Into a reaction vial charged with nitrogen were placed 0.121 grams (0.5 mmole) of 4-hydroxy-6-(4-butylphenyl) pyrimidin-2-amine and 0.178 grams (0.5 mmole) of N-phenyl trifluoromethane sulfonamide. Triethylamine 0.50 grams, (0.5 mmol) of was dissolved 0.5 mL of dry N-methyl-2-pyrolidinone, added to the mixture and the mixture heated at 60° C. for 2 hours. 2-(4-Fluorophenyl) quinoline-4,6-diamine, 0.126 grams (0.5 mmole) were dissolved in 1.0 mL of N-methyl-2-pyrolidinone and added to the reaction vial followed by 4 mole equivalents of HCl (4.0 M in dioxane). The mixture was heated at 80° C. for 10 hours whereupon a solid formed. After cooling to room temperature the entire vial contents were diluted with 10 mL of methanol and filtered. The resulting solid, N6-[2-amino-6-(4-butylphenyl)pyrimidin-4-yl]-2-(4-fluorophenyl) quinoline-4,6-diamine, was washed with 50 mL of methanol to yield 30 mg of a yellow solid (13% yield).

Method H:

Exemplary compounds disclosed herein, see Table 1, were prepared in a manner analogous to the following method which describes the preparation of N6-[2-amino-6-(4-fluorophenyl)-pyrimidin-4-yl]-2-phenyl-quinoline-4,6-diamine, the compound of Example 5.

2-Phenyl-quinoline-4,6-diamine, 0.5 grams (2.12 mmole) and 4-chloro-6-(4-fluorophenyl)pyrimidin-2-amine, 0.83 grams (4.25 mmole) were weighed directly into a reaction flask and 10 mL of dry N-methyl-2-pyrolidinone and 2 drops of concentrated hydrochloric acid was then added to the flask. The mixture was heated at 100° C. overnight under a nitrogen atmosphere. The mixture was cooled to room temperature and diluted with aqueous sodium hydroxide whereupon a dark brown solid precipitated. The solid was collected and dried under vacuum to yield 0.365 grams of N6-[2-amino-6-(4-fluorophenyl)pyrimidin-4-yl]-2-phenylquinoline-4,6-diamine (92% yield).

EXAMPLES

Exemplary compounds 1 to 125 inclusive are illustrated in Table 1 which shows the name of each compound, the molecular formula and MS result. Quinoline precursors were prepared by the method A, B, C or D as appropriate, reacted with a hydroxypyrimidine by method G, as indicated, or with a chloropyrimidine by method H, as indicated.

TABLE 1

| Ex. # | Compound Name | Method | Mol. formula | MS ion |
|---|---|---|---|---|
| 1 | N6-(2-Amino-6-methyl-pyrimidin-4-yl)-2-methyl-quinoline-4,6-diamine | H | $C_{15}H_{16}N_6$ | 281(+) |
| 2 | N6-(2-Amino-6-methyl-pyrimidin-4-yl)-2-phenyl-quinoline-4,6-diamine | H | $C_{20}H_{18}N_6$ | 343(+) |
| 3 | N6-[2-Amino-6-(2-fluoro-phenyl)-pyrimidin-4-yl]-2-phenyl-quinoline-4,6-diamine | H | $C_{25}H_{19}FN_6$ | 423(+) |
| 4 | N6-(2-Amino-6-trifluoromethyl-pyrimidin-4-yl)-2-phenyl-quinoline-4,6-diamine | H | $C_{20}H_{15}F_3N_6$ | 395(−) |
| 5 | N6-[2-Amino-6-(4-fluoro-phenyl)-pyrimidin-4-yl]-2-phenyl-quinoline-4,6-diamine | H | $C_{25}H_{19}FN_6$ | 423(+) |
| 6 | N6-[2-Amino-6-(4-chloro-phenyl)-pyrimidin-4-yl]-2-(4-fluoro-phenyl)-quinoline-4,6-diamine | H | $C_{25}H_{18}ClFN_6$ | 455/457(−) 457/459(+) |
| 7 | N6-(2-Amino-6-trifluoromethyl-pyrimidin-4-yl)-2-(4-fluoro-phenyl)-quinoline-4,6-diamine | H | $C_{20}H_{14}F_4N_6$ | 413(−) 415(+) |
| 8 | N6-[2-Amino-6-(4-trifluoromethyl-phenyl)-pyrimidin-4-yl]-2-(4-fluoro-phenyl)-quinoline-4,6-diamine | G | $C_{26}H_{18}F_4N_6$ | 491(+) |
| 9 | N6-[2-Amino-6-(4-chloro-phenyl)-pyrimidin-4-yl]-N4-benzyl-2-phenyl-quinoline-4,6-diamine | G | $C_{32}H_{25}ClN_6$ | 529/531(+) |
| 10 | 4-[2-Amino-6-(4-benzylamino-2-phenyl-quinolin-6-ylamino)-pyrimidin-4-yl]-benzonitrile | G | $C_{33}H_{25}N_7$ | 520(+) |
| 11 | 4-[2-Amino-6-(4-amino-2-methyl-quinolin-6-ylamino)-pyrimidin-4-yl]-benzonitrile | G | $C_{21}H_{17}N_7$ | 368(+) |
| 12 | N6-(2-Amino-6-trifluoromethyl-pyrimidin-4-yl)-2-methyl-quinoline-4,6-diamine | G | $C_{15}H_{13}F_3N_6$ | 335(+) |
| 13 | N6-[2-Amino-6-(4-chloro-phenyl)-pyrimidin-4-yl]-2-(3-chloro-phenyl)-quinoline-4,6-diamine | G | $C_{25}H_{18}Cl_2N_6$ | 473/475(+) |
| 14 | N6-[2-Amino-6-(2-methoxy-phenyl)-pyrimidin-4-yl]-2-(4-methoxy-phenyl)-quinoline-4,6-diamine | G | $C_{27}H_{24}N_6O_2$ | 465(+) |
| 15 | N6-[2-Amino-6-(4-chloro-phenyl)-pyrimidin-4-yl]-2-(4-methoxy-phenyl)-quinoline-4,6-diamine | G | $C_{26}H_{21}ClN_6O$ | 469/471(+) |
| 16 | N6-[2-Amino-6-(4-methoxy-phenyl)-pyrimidin-4-yl]-2-(3-chloro-phenyl)-quinoline-4,6-diamine | G | $C_{26}H_{21}ClN_6O$ | 469/471(+) |
| 17 | N6-[2-Amino-6-(2-methoxy-phenyl)-pyrimidin-4-yl]-2-(3-trifluoromethyl-phenyl)-quinoline-4,6-diamine | G | $C_{27}H_{21}F_3N_6O$ | 503(+) |
| 18 | N6-[2-Amino-6-(3-benzyloxy-phenyl)-pyrimidin-4-yl]-2-(4-methoxy-phenyl)-quinoline-4,6-diamine | G | $C_{33}H_{28}N_6O_2$ | 541(+) |
| 19 | N6-[2-Amino-6-(2-methoxy-phenyl)-pyrimidin-4-yl]-2-methyl-quinoline-4,6-diamine | G | $C_{21}H_{20}N_6O$ | 373(+) |
| 20 | N6-[2-Amino-6-(4-chloro-phenyl)-pyrimidin-4-yl]-2-methyl-quinoline-4,6-diamine | G | $C_{20}H_{17}ClN_6$ | 377(+) |
| 21 | N6-[2-Amino-6-(4-trifluoromethyl-phenyl)-pyrimidin-4-yl]-2-propoxymethyl-quinoline-4,6-diamine | G | $C_{24}H_{23}F_3N_6O$ | 469(+) |
| 22 | N6-[2-Amino-6-(3-benzyloxy-phenyl)-pyrimidin-4-yl]-2-methyl-quinoline-4,6-diamine | G | $C_{27}H_{24}N_6O$ | 449(+) |
| 23 | N6-[2-Amino-6-(3-fluoro-phenyl)-pyrimidin-4-yl]-2-pentyl-quinoline-4,6-diamine | G | $C_{24}H_{25}FN_6$ | 417(+) |
| 24 | N6-[2-Amino-6-(4-trifluoromethyl-phenyl)-pyrimidin-4-yl]-2-pentyl-quinoline-4,6-diamine | G | $C_{25}H_{25}F_3N_6$ | 467(+) |

TABLE 1-continued

| Ex. # | Compound Name | Method | Mol. formula | MS ion |
|---|---|---|---|---|
| 25 | N6-[2-Amino-6-(3-fluoro-phenyl)-pyrimidin-4-yl]-2-(2-fluoro-phenyl)-quinoline-4,6-diamine | G | $C_{25}H_{18}F_2N_6$ | 441(+) |
| 26 | N6-[2-Amino-6-(4-trifluoromethyl-phenyl)-pyrimidin-4-yl]-2-(2-fluoro-phenyl)-quinoline-4,6-diamine | G | $C_{26}H_{18}F_4N_6$ | 491(+) |
| 27 | N6-[2-Amino-6-(3-fluoro-phenyl)-pyrimidin-4-yl]-2-(4-methoxy-phenyl)-quinoline-4,6-diamine | G | $C_{26}H_{21}FN_6O$ | 453(+) |
| 28 | N6-[2-Amino-6-(4-trifluoromethyl-phenyl)-pyrimidin-4-yl]-2-(4-methoxy-phenyl)-quinoline-4,6-diamine | G | $C_{27}H_{21}F_3N_6O$ | 503(+) |
| 29 | N6-[2-Amino-6-(4-methoxy-phenyl)-pyrimidin-4-yl]-2-(2-chloro-phenyl)-quinoline-4,6-diamine | G | $C_{26}H_{21}ClN_6O$ | 469/471(+) |
| 30 | N6-[2-Amino-6-(4-trifluoromethyl-phenyl)-pyrimidin-4-yl]-2-(2-chloro-phenyl)-quinoline-4,6-diamine | G | $C_{26}H_{18}ClF_3N_6$ | 507/508(+) |
| 31 | N6-[2-Amino-6-(3-fluoro-phenyl)-pyrimidin-4-yl]-2-(3-chloro-phenyl)-quinoline-4,6-diamine | G | $C_{25}H_{18}ClFN_6$ | 457/459(+) |
| 32 | N6-[2-Amino-6-(2-methoxy-phenyl)-pyrimidin-4-yl]-2-(3-chloro-phenyl)-quinoline-4,6-diamine | G | $C_{26}H_{21}ClN_6O$ | 469/471(+) |
| 33 | N6-[2-Amino-6-(4-methoxy-phenyl)-pyrimidin-4-yl]-2-(3-trifluoromethyl-phenyl)-quinoline-4,6-diamine | G | $C_{27}H_{21}F_3N_6O$ | 503(+) |
| 34 | N6-[2-Amino-6-(4-chloro-phenyl)-pyrimidin-4-yl]-2-(3-trifluoromethyl-phenyl)-quinoline-4,6-diamine | G | $C_{26}H_{18}ClF_3N_6$ | 507/509(+) |
| 35 | N6-[2-Amino-6-(3-fluoro-phenyl)-pyrimidin-4-yl]-2-(4-trifluoromethyl-phenyl)-quinoline-4,6-diamine | G | $C_{26}H_{18}F_4N_6$ | 491(+) |
| 36 | N6-[2-Amino-6-(4-trifluoromethyl-phenyl)-pyrimidin-4-yl]-2-(4-trifluoromethyl-phenyl)-quinoline-4,6-diamine | G | $C_{27}H_{18}F_6N_6$ | 541(+) |
| 37 | N6-[2-Amino-6-(4-trifluoromethyl-phenyl)-pyrimidin-4-yl]-2-methyl-quinoline-4,6-diamine | G | $C_{21}H_{17}F_3N_6$ | 411(+) |
| 38 | N6-(2-Amino-6-propoxymethyl-pyrimidin-4-yl)-2-(3-chloro-phenyl)-quinoline-4,6-diamine | G | $C_{23}H_{23}ClN_6O$ | 435/437(+) |
| 39 | N6-(2-Amino-6-propoxymethyl-pyrimidin-4-yl)-2-(3-trifluoromethyl-phenyl)-quinoline-4,6-diamine | G | $C_{24}H_{23}F_3N_6O$ | 469(+) |
| 40 | N6-[2-Amino-6-(4-phenoxymethyl-phenyl)-pyrimidin-4-yl]-2-(4-trifluoromethyl-phenyl)-quinoline-4,6-diamine | G | $C_{33}H_{25}F_3N_6O$ | 579(+) |
| 41 | N6-[2-Amino-6-(3-phenoxymethyl-phenyl)-pyrimidin-4-yl]-2-(2-chloro-phenyl)-quinoline-4,6-diamine | G | $C_{32}H_{25}ClN_6O$ | 545/547(+) |
| 42 | N6-(2-Amino-6-isopropoxymethyl-pyrimidin-4-yl)-2-(3-chloro-phenyl)-quinoline-4,6-diamine | G | $C_{23}H_{23}ClN_6O$ | 435/437(+) |
| 43 | N6-[2-Amino-6-(4-benzyloxy-phenyl)-pyrimidin-4-yl]-2-methyl-quinoline-4,6-diamine | G | $C_{27}H_{24}N_6O$ | 449(+) |
| 44 | N6-[2-Amino-6-(3-chloro-phenyl)-pyrimidin-4-yl]-2-phenyl-quinoline-4,6-diamine | G | $C_{25}H_{19}ClN_6$ | 439/441(+) |
| 45 | N6-[2-Amino-6-(3-chloro-phenyl)-pyrimidin-4-yl]-2-(2-fluoro-phenyl)-quinoline-4,6-diamine | G | $C_{25}H_{18}ClFN_6$ | 457/459(+) |
| 46 | N6-[2-Amino-6-(4-methoxy-phenyl)-pyrimidin-4-yl]-2-(4-fluoro-phenyl)-quinoline-4,6-diamine | G | $C_{26}H_{21}FN_6O$ | 453(+) |
| 47 | N6-[2-Amino-6-(3-chloro-phenyl)-pyrimidin-4-yl]-2-(4-fluoro-phenyl)-quinoline-4,6-diamine | G | $C_{25}H_{18}ClFN_6$ | 457/459(+) |
| 48 | N6-[2-Amino-6-(4-methoxy-phenyl)-pyrimidin-4-yl]-2-(4-methoxy-phenyl)-quinoline-4,6-diamine | G | $C_{27}H_{24}N_6O_2$ | 465(+) |
| 49 | N6-[2-Amino-6-(3-chloro-phenyl)-pyrimidin-4-yl]-2-(4-methoxy-phenyl)-quinoline-4,6-diamine | G | $C_{26}H_{21}ClN_6O$ | 469/471(+) |

TABLE 1-continued

| Ex. # | Compound Name | Method | Mol. formula | MS ion |
|---|---|---|---|---|
| 50 | N6-[2-Amino-6-(3-chloro-phenyl)-pyrimidin-4-yl]-2-(4-trifluoromethyl-phenyl)-quinoline-4,6-diamine | G | $C_{26}H_{18}ClF_3N_6$ | 507/509(+) |
| 51 | N6-[2-Amino-6-(4-benzyloxy-phenyl)-pyrimidin-4-yl]-2-phenyl-quinoline-4,6-diamine | G | $C_{32}H_{26}N_6O$ | 511(+) |
| 52 | N6-[2-Amino-6-(3-benzyloxy-phenyl)-pyrimidin-4-yl]-2-(4-trifluoromethyl-phenyl)-quinoline-4,6-diamine | G | $C_{33}H_{25}F_3N_6O$ | 579(+) |
| 53 | N6-[2-Amino-6-(3-benzyloxy-phenyl)-pyrimidin-4-yl]-2-(4-fluoro-phenyl)-quinoline-4,6-diamine | G | $C_{32}H_{25}FN_6O$ | 529(+) |
| 54 | N6-[2-Amino-6-(3-benzyloxy-phenyl)-pyrimidin-4-yl]-2-(2-fluoro-phenyl)-quinoline-4,6-diamine | G | $C_{32}H_{25}FN_6O$ | 529(+) |
| 55 | N6-[2-Amino-6-(4-benzyloxy-phenyl)-pyrimidin-4-yl]-2-(4-fluoro-phenyl)-quinoline-4,6-diamine | G | $C_{32}H_{25}FN_6O$ | 529(+) |
| 56 | N6-[2-Amino-6-(4-benzyloxy-phenyl)-pyrimidin-4-yl]-2-(4-methoxy-phenyl)-quinoline-4,6-diamine | G | $C_{33}H_{28}N_6O_2$ | 541(+) |
| 57 | N6-[2-Amino-6-(4-chloro-phenyl)-pyrimidin-4-yl]-2-(2-fluoro-phenyl)-quinoline-4,6-diamine | G | $C_{25}H_{18}ClFN_6$ | 457/459(+) |
| 58 | N6-[2-Amino-6-(2-methoxy-phenyl)-pyrimidin-4-yl]-2-(4-cyclohexyl-phenyl)-quinoline-4,6-diamine | G | $C_{32}H_{32}N_6O$ | 517(+) |
| 59 | N6-[2-Amino-6-(2-fluoro-phenyl)-pyrimidin-4-yl]-2-(4-fluoro-phenyl)-quinoline-4,6-diamine | G | $C_{25}H_{18}F_2N_6$ | 441(+) |
| 60 | N6-[2-Amino-6-(4-chloro-phenyl)-pyrimidin-4-yl]-2-(3-methoxy-phenyl)-quinoline-4,6-diamine | G | $C_{26}H_{21}ClN_6O$ | 469/471(+) |
| 61 | N6-[2-Amino-6-(4-trifluoromethyl-phenyl)-pyrimidin-4-yl]-2-(3-methoxy-phenyl)-quinoline-4,6-diamine | G | $C_{27}H_{21}F_3N_6O$ | 503(+) |
| 62 | N6-[2-Amino-6-(2-methoxy-phenyl)-pyrimidin-4-yl]-2-(4-chloro-phenyl)-quinoline-4,6-diamine | G | $C_{26}H_{21}ClN_6O$ | 469/471(+) |
| 63 | N6-[2-Amino-6-(4-trifluoromethyl-phenyl)-pyrimidin-4-yl]-2-(3-trifluoromethyl-phenyl)-quinoline-4,6-diamine | G | $C_{27}H_{18}F_6N_6$ | 541(+) |
| 64 | N6-[2-Amino-6-(2-methoxy-phenyl)-pyrimidin-4-yl]-2-(4-trifluoromethyl-phenyl)-quinoline-4,6-diamine | G | $C_{27}H_{21}F_3N_6O$ | 503(+) |
| 65 | N6-[2-Amino-6-(4-chloro-phenyl)-pyrimidin-4-yl]-2-(4-trifluoromethyl-phenyl)-quinoline-4,6-diamine | G | $C_{26}H_{18}ClF_3N_6$ | 507/509(+) |
| 66 | N6-[2-Amino-6-(2-fluoro-phenyl)-pyrimidin-4-yl]-2-methyl-quinoline-4,6-diamine | G | $C_{20}H_{17}FN_6$ | 361(+) |
| 67 | N6-[2-Amino-6-(3-benzyloxy-phenyl)-pyrimidin-4-yl]-2-(4-chloro-phenyl)-quinoline-4,6-diamine | G | $C_{32}H_{25}ClN_6O$ | 545/547(+) |
| 68 | N6-[2-Amino-6-(3-benzyloxy-phenyl)-pyrimidin-4-yl]-2-phenyl-quinoline-4,6-diamine | G | $C_{32}H_{26}N_6O$ | 511(+) |
| 69 | N6-[2-Amino-6-(3-fluoro-phenyl)-pyrimidin-4-yl]-2-phenyl-quinoline-4,6-diamine | G | $C_{25}H_{19}FN_6$ | 423(+) |
| 70 | N6-[2-Amino-6-(4-trifluoromethyl-phenyl)-pyrimidin-4-yl]-2-(4-cyclohexyl-phenyl)-quinoline-4,6-diamine | G | $C_{32}H_{29}F_3N_6$ | 555(+) |
| 71 | N6-[2-Amino-6-(4-benzyloxy-phenyl)-pyrimidin-4-yl]-2-(4-cyclohexyl-phenyl)-quinoline-4,6-diamine | G | $C_{38}H_{36}N_6O$ | 593(+) |
| 72 | N6-[2-Amino-6-(4-chloro-phenyl)-pyrimidin-4-yl]-2-(4-cyclohexyl-phenyl)-quinoline-4,6-diamine | G | $C_{31}H_{29}ClN_6$ | 521/523(+) |
| 73 | N6-[2-Amino-6-(4-benzyloxy-phenyl)-pyrimidin-4-yl]-2-(4-chloro-phenyl)-quinoline-4,6-diamine | G | $C_{32}H_{25}ClN_6O$ | 545/547(+) |
| 74 | N6-[2-Amino-6-(3-fluoro-phenyl)-pyrimidin-4-yl]-2-methyl-quinoline-4,6-diamine | G | $C_{20}H_{17}FN_6$ | 361(+) |

TABLE 1-continued

| Ex. # | Compound Name | Method | Mol. formula | MS ion |
|---|---|---|---|---|
| 75 | N6-[2-Amino-6-(2-methoxy-phenyl)-pyrimidin-4-yl]-2-phenyl-quinoline-4,6-diamine | G | $C_{26}H_{22}N_6O$ | 435(+) |
| 76 | N6-[2-Amino-6-(3-fluoro-phenyl)-pyrimidin-4-yl]-2-(3-trifluoromethyl-phenyl)-quinoline-4,6-diamine | G | $C_{26}H_{18}F_4N_6$ | 491(+) |
| 77 | N6-[2-Amino-6-(4-methoxy-phenyl)-pyrimidin-4-yl]-2-phenyl-quinoline-4,6-diamine | G | $C_{26}H_{22}N_6O$ | 435(+) |
| 78 | N6-(2-Amino-6-pentyl-pyrimidin-4-yl)-2-(4-fluoro-phenyl)-quinoline-4,6-diamine | G | $C_{24}H_{25}FN_6$ | 417(+) |
| 79 | N6-[2-Amino-6-(4-methoxy-phenyl)-pyrimidin-4-yl]-2-(3-methoxy-phenyl)-quinoline-4,6-diamine | G | $C_{27}H_{24}N_6O_2$ | 465(+) |
| 80 | N6-(2-Amino-6-trifluoromethyl-pyrimidin-4-yl)-2-(4-methoxy-phenyl)-quinoline-4,6-diamine | G | $C_{21}H_{17}F_3N_6O$ | 427(+) |
| 81 | N6-(2-Amino-6-pentyl-pyrimidin-4-yl)-2-(3-chloro-phenyl)-quinoline-4,6-diamine | G | $C_{24}H_{25}ClN_6$ | 433/435(+) |
| 82 | N6-(2-Amino-6-trifluoromethyl-pyrimidin-4-yl)-2-(3-chloro-phenyl)-quinoline-4,6-diamine | G | $C_{20}H_{14}ClF_3N_6$ | 431/433(+) |
| 83 | N6-(2-Amino-6-pentyl-pyrimidin-4-yl)-2-(4-chloro-phenyl)-quinoline-4,6-diamine | G | $C_{24}H_{25}ClN_6$ | 433/435(+) |
| 84 | N6-(2-Amino-6-benzyloxy-pyrimidin-4-yl)-2-(4-fluoro-phenyl)-quinoline-4,6-diamine | G | $C_{26}H_{21}FN_6O$ | 453(+) |
| 85 | N6-(2-Amino-6-phenoxymethyl-pyrimidin-4-yl)-2-methyl-quinoline-4,6-diamine | G | $C_{21}H_{20}N_6O$ | 371(−) |
| 86 | N6-(2-Amino-6-phenoxymethyl-pyrimidin-4-yl)-2-(3-chloro-phenyl)-quinoline-4,6-diamine | G | $C_{26}H_{21}ClN_6O$ | 469/471(+) |
| 87 | N6-[2-Amino-6-(3-fluoro-phenyl)-pyrimidin-4-yl]-2-(4-cyclohexyl-phenyl)-quinoline-4,6-diamine | G | $C_{31}H_{29}FN_6$ | 505(+) |
| 88 | N6-(2-Amino-6-trifluoromethyl-pyrimidin-4-yl)-2-(4-chloro-phenyl)-quinoline-4,6-diamine | G | $C_{20}H_{14}ClF_3N_6$ | 431/433(+) |
| 89 | N6-[2-Amino-6-(2-methoxy-phenyl)-pyrimidin-4-yl]-2-(4-fluoro-phenyl)-quinoline-4,6-diamine | G | $C_{26}H_{21}FN_6O$ | 453(+) |
| 90 | N6-[2-Amino-6-(3-fluoro-phenyl)-pyrimidin-4-yl]-2-(3-methoxy-phenyl)-quinoline-4,6-diamine | G | $C_{26}H_{21}FN_6O$ | 453(+) |
| 91 | N6-[2-Amino-6-(3-chloro-phenyl)-pyrimidin-4-yl]-2-(3-chloro-phenyl)-quinoline-4,6-diamine | G | $C_{25}H_{18}Cl_2N_6$ | 473/475(+) |
| 92 | N6-[2-Amino-6-(4-trifluoromethyl-phenyl)-pyrimidin-4-yl]-2-(3-chloro-phenyl)-quinoline-4,6-diamine | G | $C_{26}H_{18}ClF_3N_6$ | 507/509(+) |
| 93 | N6-[2-Amino-6-(3-fluoro-phenyl)-pyrimidin-4-yl]-2-(4-chloro-phenyl)-quinoline-4,6-diamine | G | $C_{25}H_{18}ClFN_6$ | 457/459(+) |
| 94 | N6-[2-Amino-6-(3-chloro-phenyl)-pyrimidin-4-yl]-2-(4-chloro-phenyl)-quinoline-4,6-diamine | G | $C_{25}H_{18}Cl_2N_6$ | 473/475(+) |
| 95 | N6-[2-Amino-6-(4-trifluoromethyl-phenyl)-pyrimidin-4-yl]-2-(4-chloro-phenyl)-quinoline-4,6-diamine | G | $C_{26}H_{18}ClF_3N_6$ | 507/509(+) |
| 96 | N6-[2-Amino-6-(3-chloro-phenyl)-pyrimidin-4-yl]-2-methyl-quinoline-4,6-diamine | G | $C_{20}H_{17}ClN_6$ | 377/379(+) |
| 97 | N6-[2-Amino-6-(3-chloro-phenyl)-pyrimidin-4-yl]-2-(4-cyclohexyl-phenyl)-quinoline-4,6-diamine | G | $C_{31}H_{29}ClN_6$ | 521/523(+) |
| 98 | N6-[2-Amino-6-(3-benzyloxy-phenyl)-pyrimidin-4-yl]-2-(4-cyclohexyl-phenyl)-quinoline-4,6-diamine | G | $C_{38}H_{36}N_6O$ | 593(+) |
| 99 | N6-(2-Amino-6-benzyloxy-pyrimidin-4-yl)-2-(3-fluoro-phenyl)-quinoline-4,6-diamine | G | $C_{26}H_{21}FN_6O$ | 453(+) |

TABLE 1-continued

| Ex. # | Compound Name | Method | Mol. formula | MS ion |
|---|---|---|---|---|
| 100 | N6-[2-Amino-6-(3-benzyloxy-phenyl)-pyrimidin-4-yl]-2-(3-fluoro-phenyl)-quinoline-4,6-diamine | G | $C_{32}H_{25}FN_6O$ | 529(+) |
| 101 | N6-[2-Amino-6-(4-butyl-phenyl)-pyrimidin-4-yl]-2-(4-cyclohexyl-phenyl)-quinoline-4,6-diamine | G | $C_{35}H_{38}N_6$ | 543(+) |
| 102 | N6-[2-Amino-6-(2-methoxy-phenyl)-pyrimidin-4-yl]-2-pentyl-quinoline-4,6-diamine | G | $C_{25}H_{28}N_6O$ | 429(+) |
| 103 | N6-[2-Amino-6-(2-fluoro-phenyl)-pyrimidin-4-yl]-2-(3-fluoro-phenyl)-quinoline-4,6-diamine | G | $C_{25}H_{18}F_2N_6$ | 441(+) |
| 104 | N6-[2-Amino-6-(3-fluoro-phenyl)-pyrimidin-4-yl]-2-(3-fluoro-phenyl)-quinoline-4,6-diamine | G | $C_{25}H_{18}F_2N_6$ | 441(+) |
| 105 | N6-[2-Amino-6-(2-methoxy-phenyl)-pyrimidin-4-yl]-2-(3-fluoro-phenyl)-quinoline-4,6-diamine | G | $C_{26}H_{21}FN_6O$ | 453(+) |
| 106 | N6-[2-Amino-6-(3-chloro-phenyl)-pyrimidin-4-yl]-2-(3-fluoro-phenyl)-quinoline-4,6-diamine | G | $C_{25}H_{18}ClFN_6$ | 457/459(+) |
| 107 | N6-[2-Amino-6-(4-chloro-phenyl)-pyrimidin-4-yl]-2-(3-fluoro-phenyl)-quinoline-4,6-diamine | G | $C_{25}H_{18}ClFN_6$ | 457/459(+) |
| 108 | N6-(2-Amino-6-trifluoromethyl-pyrimidin-4-yl)-2-(3-fluoro-phenyl)-quinoline-4,6-diamine | G | $C_{20}H_{14}F_4N_6$ | 415(+) |
| 109 | N6-[2-Amino-6-(4-trifluoromethyl-phenyl)-pyrimidin-4-yl]-2-(3-fluoro-phenyl)-quinoline-4,6-diamine | G | $C_{26}H_{18}F_4N_6$ | 491(+) |
| 110 | N6-[2-Amino-6-(2-chloro-phenyl)-pyrimidin-4-yl]-2-(4-fluoro-phenyl)-quinoline-4,6-diamine | G | $C_{25}H_{18}ClFN_6$ | 457/459(+) |
| 111 | N6-[2-Amino-6-(4-butyl-phenyl)-pyrimidin-4-yl]-2-(4-fluoro-phenyl)-quinoline-4,6-diamine | G | $C_{29}H_{27}FN_6$ | 479(+) |
| 112 | N6-[2-Amino-6-(2-chloro-phenyl)-pyrimidin-4-yl]-2-(3-chloro-phenyl)-quinoline-4,6-diamine | G | $C_{25}H_{18}Cl_2N_6$ | 473/475(+) |
| 113 | N6-[2-Amino-6-(2-chloro-phenyl)-pyrimidin-4-yl]-2-(4-chloro-phenyl)-quinoline-4,6-diamine | G | $C_{25}H_{18}Cl_2N_6$ | 473/475(+) |
| 114 | N6-[2-Amino-6-(2-chloro-phenyl)-pyrimidin-4-yl]-2-(3-trifluoromethyl-phenyl)-quinoline-4,6-diamine | G | $C_{26}H_{18}ClF_3N_6$ | 507/509(+) |
| 115 | N6-[2-Amino-6-(2-fluoro-phenyl)-pyrimidin-4-yl]-2-(4-trifluoromethyl-phenyl)-quinoline-4,6-diamine | G | $C_{26}H_{18}F_4N_6$ | 491(+) |
| 116 | N6-[2-Amino-6-(4-butyl-phenyl)-pyrimidin-4-yl]-2-(4-trifluoromethyl-phenyl)-quinoline-4,6-diamine | G | $C_{30}H_{27}F_3N_6$ | 529(+) |
| 117 | N6-[2-Amino-6-(4-butyl-phenyl)-pyrimidin-4-yl]-2-(4-chloro-phenyl)-quinoline-4,6-diamine | G | $C_{29}H_{27}ClN_6$ | 495/497(+) |
| 118 | N6-[2-Amino-6-(2-ethoxy-4-fluoro-phenyl)-pyrimidin-4-yl]-2-(3-fluoro-phenyl)-quinoline-4,6-diamine | G | $C_{27}H_{22}F_2N_6O$ | 485(+) |
| 119 | N6-[2-Amino-6-(2-chloro-phenyl)-pyrimidin-4-yl]-2-(3-fluoro-phenyl)-quinoline-4,6-diamine | G | $C_{25}H_{18}ClFN_6$ | 457/459(+) |
| 120 | N6-[2-Amino-6-(3-trifluoromethyl-phenyl)-pyrimidin-4-yl]-2-(3-fluoro-phenyl)-quinoline-4,6-diamine | G | $C_{26}H_{18}F_4N_6$ | 491(+) |
| 121 | N6-[2-Amino-6-(2-fluoro-phenyl)-pyrimidin-4-yl]-2-(4-chloro-phenyl)-quinoline-4,6-diamine | G | $C_{25}H_{18}ClFN_6$ | 457/459(+) |
| 122 | N6-[2-Amino-6-(4-bromo-phenyl)-pyrimidin-4-yl]-2-(4-fluoro-phenyl)-quinoline-4,6-diamine | G | $C_{25}H_{18}BrFN_6$ | 501/503(+) |
| 123 | N6-[2-Amino-6-(2-chloro-phenyl)-pyrimidin-4-yl]-2-(4-cyclohexyl-phenyl)-quinoline-4,6-diamine | G | $C_{31}H_{29}ClN_6$ | 521/523(+) |
| 124 | N6-[2-Amino-6-(2-ethoxy-4-fluoro-phenyl)-pyrimidin-4-yl]-2-(3-fluoro-phenyl)-N4,N4-dimethyl-quinoline-4,6-diamine | G | $C_{29}H_{26}F_2N_6O$ | 513(+) |

TABLE 1-continued

| Ex. # | Compound Name | Method | Mol. formula | MS ion |
|---|---|---|---|---|
| 125 | N6-[2-Amino-6-(2-fluoro-phenyl)-pyrimidin-4-yl]-2-(3-fluoro-phenyl)-N4,N4-dimethyl-quinoline-4,6-diamine | G | $C_{27}H_{22}F_2N_6$ | 469(+) |

What is claimed is:

1. A compound in accord with structural diagram I,

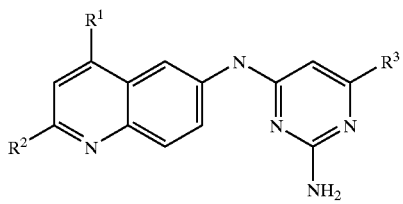

wherein:
R$^1$ is NE$^1$E$^2$ where E$^1$ is selected from hydrogen and methyl and E$^2$ is selected from hydrogen, C$_{1-4}$alkyl and phenylC$_{1-4}$alkyl;
R$^2$ is selected from E$^3$ and E$^4$, wherein:
E$^3$ is selected from C$_{1-6}$alkyl, C$_{1-4}$ alkoxy and C$_{1-6}$alkoxyC$_{1-4}$alkyl; and
E$^4$ is phenyl substituted with a moiety selected from halogen, C$_{1-4}$alkyl, C$_{1-4}$alkoxy, perfluoroC$_{1-2}$alkyl and C$_{5-7}$cycloalkyl;
R$^3$ is selected from E$^5$ and E$^6$, wherein:
E$^5$ is selected from NH$_2$, perfluoroC$_{1-2}$alkyl, C$_{1-6}$alkyl, C$_{1-6}$alkoxyC$_{1-4}$alkyl, phenylC$_{1-2}$alkoxy and phenoxyC$_{1-2}$alkyl; and
E$^6$ is phenyl substituted at one or two positions with moieties independently selected from halogen, cyano, perfluoroC$_{1-2}$alkyl, C$_{1-4}$alkoxy, phenylC$_{1-2}$alkoxy, phenoxyC$_{1-2}$alkyl, C$_{1-6}$alkoxyC$_{1-4}$alkyl or a pharmaceutically-acceptable salt thereof.

2. A compound according to claim 1, wherein:
R$^1$ is NE$^1$E$^2$ where E$^1$ is hydrogen and E$^2$ is selected from hydrogen, methyl and benzyl;
R$^2$ is selected from E$^3$ and E$^4$, wherein:
E$^3$ is selected from methyl, pentyl, propoxymethyl; and
E$^4$ is phenyl substituted with a moiety selected from fluoro, chloro, methyl, methoxy, trifluoromethyl and cyclohexyl;
R$^3$ selected from E$^5$ and E$^6$, wherein:
E$^5$ is selected from methyl, pentyl, trifluoromethyl, propoxymethyl, benzyloxy and phenyloxymethyl; and
E$^6$ is phenyl substituted at one or two positions with moieties independently selected from chloro, fluoro, butyl, trifluoromethyl, methoxy, ethoxy, benzyloxy, phenoxymethyl, propoxymethyl and cyano.

3. A method for the treatment of pain in a subject suffering therefrom, comprising:
administering to said subject a pain-ameliorating effective amount of a compound according to claim 1.

4. A pharmaceutical composition comprising a therapeutically-effective amount of a compound according to claim 1 together with a pharmaceutically-acceptable excipient or diluent.

5. A method for preparing compounds according to claim 1, said method comprising:
a) preparing hydroxy-pyrimidine precursors according to structural diagram II,

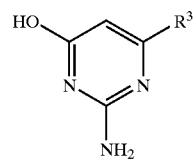

by reacting a 3-substituted-3-oxo-propionic ethyl ester with guanidine hydrochloride in N-dimethylformamide in the presence of sodium hydride and activated 5 Å molecular seives;

b) preparing chloro-pyrimidine precursors by chlorinating a hydroxy-pyrimidine compound according to structural diagram II by refluxing with phosphoryloxychloride and phosphorus pentachloride to form a compound in according to structural diagram III,

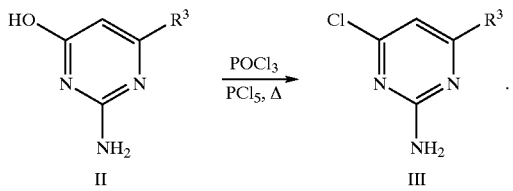

c) preparing triflate-pyrimidine precursors by reacting a hydroxy-pyrimidine compound according to structural diagram II by heating with N-phenyl trifluoromethane sulfonamide, triethylamine and dry N-methyl-2-pyrolidinone to form a compound in according to structural diagram IV,

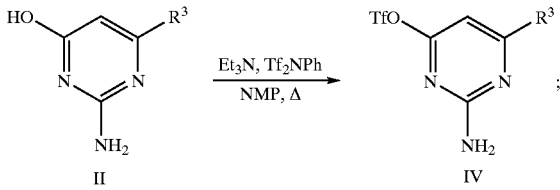

d) preparing quinoline precursors according to the following process;
d1) preparing novel 3-substituted-3-oxo-propionic acid ethyl esters (β-keto esters) according to structural diagram V, as follows:

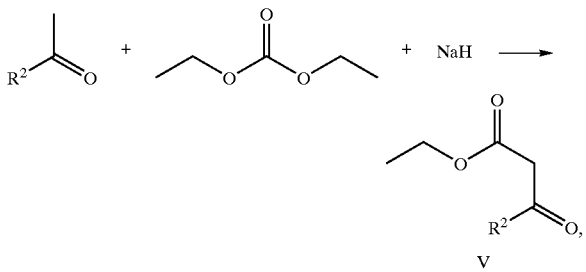

wherein R$^2$ as heretofore defined;

d2) converting said β-keto esters of structural diagram V to enamines according to structural diagram VI, as follows

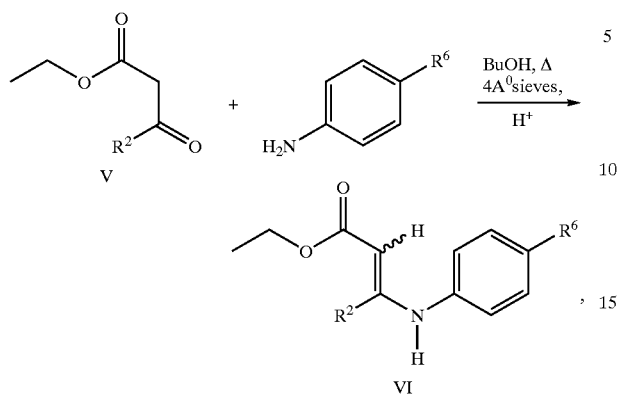

wherein $R^6$ is a group selected from —NH—CO—CH$_3$ or NO$_2$;

d3) cyclizing said enamines of structural diagram VI to form compounds according to structural diagram VII, as follows

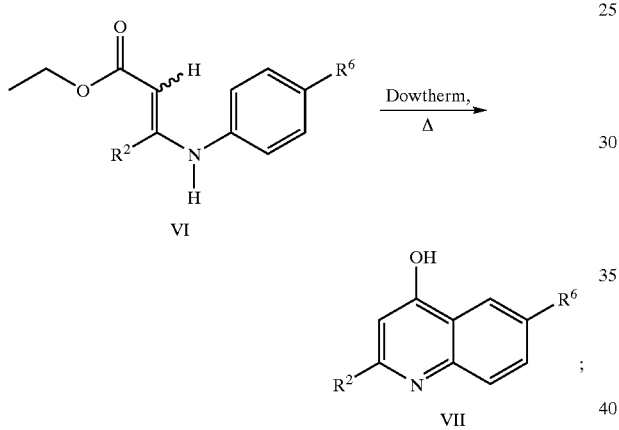

and d4) when $R^6$ is —NH—CO—CH$_3$, converting a compound of structural diagram VII to a compound according to structural diagram I by the process of the following scheme:

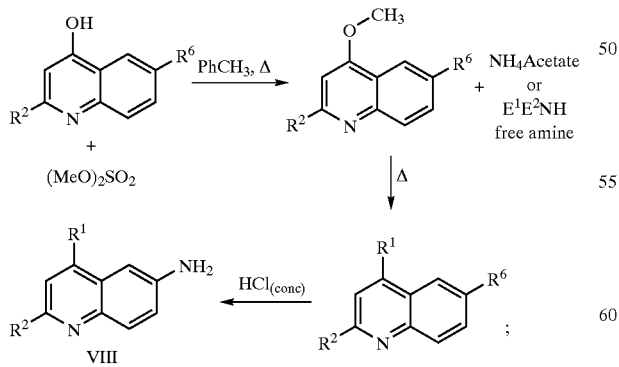

or,
when $R^6$ is —NO$_2$, converting a compound of structural diagram VII to a compound according to structural diagram I as follows:

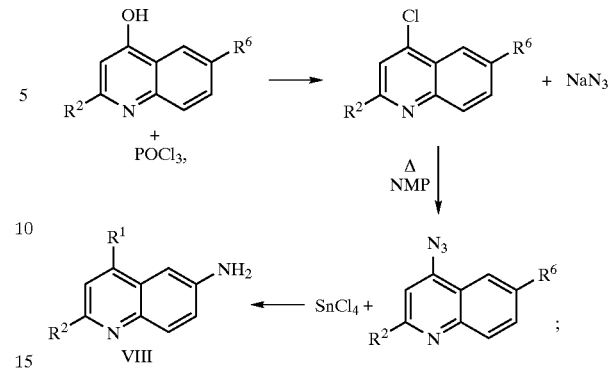

or, alternatively,
when $R^6$ is —NO$_2$, converting a compound of structural diagram VII to a compound according to structural diagram I as follows:

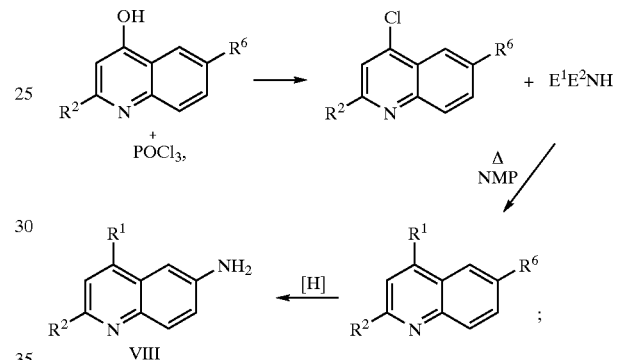

e) reacting a quinoline precursor of structure VIII with a chloro-pyrimidine precursor of structure III according to the following scheme to form a compound according to structural diagram I:

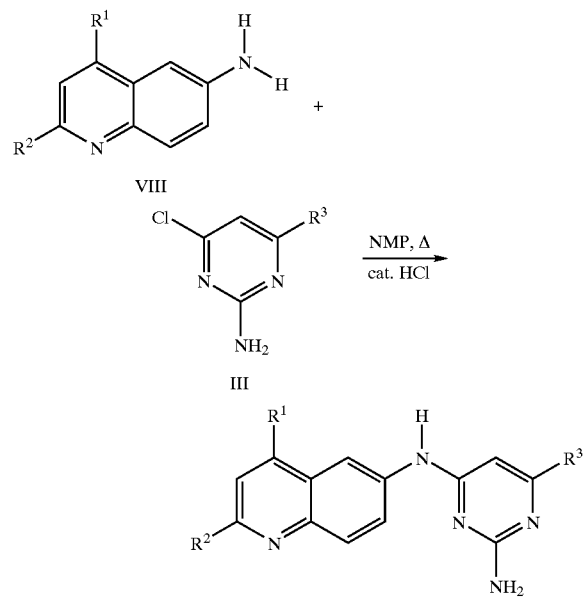

or, f) reacting a quinoline precursor of structure VIII with a triflate-pyrimidine precursor of structure IV according to the following scheme to form a compound according to structural diagram I:

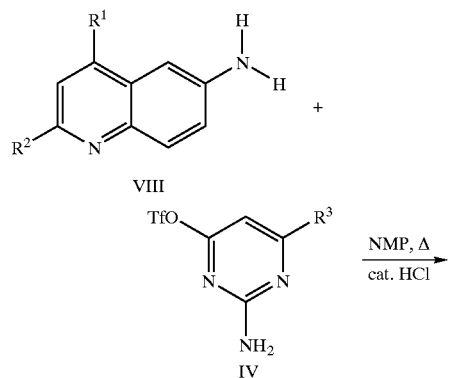

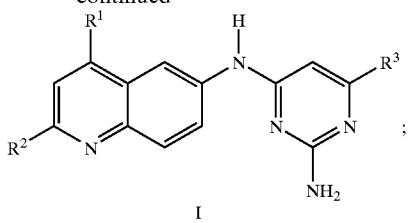

wherein, if necessary, in steps a), b), c), d), e) and f) any functional group is protected with a protecting group, and thereafter, g) removing any said protecting group;
h) if necessary converting one compound according to structural diagram I to another compound according to structural diagram I, and
i) purifying said compound of structural diagram I to the extent necessary and, if necessary, forming a pharmaceutically-acceptable salt.

\* \* \* \* \*